(12) United States Patent
Hammer et al.

(10) Patent No.: US 6,348,176 B1
(45) Date of Patent: Feb. 19, 2002

(54) CARTRIDGE-BASED ANALYTICAL INSTRUMENT USING CENTRIFUGAL FORCE/PRESSURE FOR METERING/ TRANSPORT OF FLUIDS

(75) Inventors: Roger Hammer, Knightstown; William Reid, Noblesville; David Storvick, Indpls; Richard A. Riedel, Carmel; James S. Hutchinson; Daniel Kennedy, both of Indianapolis, all of IN (US); Douglas E. Boyd, Dublin, OH (US); James Ramey, Greenwood; John W. Stoughton, Indianapolis, both of IN (US); Glen T. Mathews, San Diego, CA (US)

(73) Assignee: Careside, Inc., Culver City, CA (US)

( * ) Notice: Subject to any disclaimer, the term of this patent is extended or adjusted under 35 U.S.C. 154(b) by 0 days.

(21) Appl. No.: 09/248,737

(22) Filed: Feb. 11, 1999

(51) Int. Cl.[7] ............................................... G01N 21/00
(52) U.S. Cl. ............................. 422/64; 422/66; 422/67; 422/68.1; 422/72
(58) Field of Search .............................. 422/63–67, 72, 422/68.1

(56) References Cited

U.S. PATENT DOCUMENTS

| | | | |
|---|---|---|---|
| 3,555,284 A | 1/1971 | Anderson | 250/218 |
| 3,586,484 A | 6/1971 | Anderson | 23/230 |
| 3,684,450 A | 8/1972 | Adler et al. | 23/230 |
| 4,284,602 A * | 8/1981 | Kelton et al. | 422/72 |
| 4,309,384 A | 1/1982 | Trod | 422/64 |
| 4,390,499 A * | 6/1983 | Curtis et al. | 422/72 |
| 4,412,973 A | 11/1983 | Guigan | 422/72 |
| 4,676,952 A * | 6/1987 | Edelmann et al. | 422/72 |
| 4,690,801 A | 9/1987 | Anderson | 422/68 |
| 4,690,899 A * | 9/1987 | Klose et al. | 436/45 |
| 4,708,940 A | 11/1987 | Yoshida et al. | 436/45 |
| 4,740,472 A | 4/1988 | Burtis et al. | 436/63 |

(List continued on next page.)

FOREIGN PATENT DOCUMENTS

EP 0 160 282 1/1990

*Primary Examiner*—Arlen Soderquist
(74) *Attorney, Agent, or Firm*—Shapiro, Borenstein & Dupont LLP

(57) ABSTRACT

An analytical instrument for analyzing fluids. The instrument includes a cartridge carousel assembly which receives analytical cartridges. The analytical cartridges include a centrifugal force-operated sample metering/separation system, a pressure-operated sample transport system, and a test element which provides a detectable analytical property of a fluid sample. The cartridge carousel assembly includes a cartridge rotor plate which has a plurality of cartridge ports which receive the cartridges. A rotary drive mechanism rotates the cartridge rotor plate to provide rotation of the plate which activates the centrifugal force-operated sample metering/separation system of the cartridge. The instrument includes a sample transport actuator which activates the pressure-operated sample transport system of the cartridge. In addition, the instrument includes a detector which measures the detectable analytical property of the fluid sample after the sample metering and transport systems have been activated. The instrument includes tracking and control systems which track and control the rotary drive mechanism and sample transport actuator to provide coordinated operation of the centrifugal force-operated sample metering/ separation system and the pressure operated sample transport system wherein the coordinated operation provides delivery of a metered amount of sample to the test element of the test cartridge. Further, the tracking and control unit includes a user-input interface for receiving data input from a user of the instrument, a central processing unit, a real-time processor, and a data output interface which provides output of results of the measurements made by the instrument.

13 Claims, 27 Drawing Sheets

U.S. PATENT DOCUMENTS

| | | | |
|---|---|---|---|
| 4,777,141 A | 10/1988 | Calzi et al. | 436/69 |
| 4,788,154 A | 11/1988 | Guigan | 436/180 |
| 4,814,144 A | 3/1989 | Edelmann et al. | 422/102 |
| 4,814,282 A | 3/1989 | Holen et al. | 436/165 |
| 4,837,160 A | 6/1989 | Meserol et al. | 436/45 |
| 4,865,810 A | 9/1989 | Simon | 422/72 |
| 4,883,763 A | 11/1989 | Holen et al. | 436/45 |
| 4,898,832 A | 2/1990 | Klose et al. | 436/45 |
| 4,902,479 A | 2/1990 | Bri kus | 422/72 |
| 4,937,050 A | 6/1990 | Meinecke et al. | 422/68.1 |
| 4,940,527 A | 7/1990 | Kazlauskas et al. | 204/401 |
| 4,956,148 A | 9/1990 | Grandone | 422/64 |
| 4,970,053 A | 11/1990 | Fechtner | 422/102 |
| 5,001,417 A | 3/1991 | Pumphrey et al. | 324/71.5 |
| 5,035,861 A | 7/1991 | Grandone | 422/64 |
| 5,061,381 A | 10/1991 | Burd | 210/789 |
| 5,061,446 A | 10/1991 | Guigan | 422/64 |
| 5,077,013 A | 12/1991 | Guigan | 422/64 |
| 5,089,417 A | 2/1992 | Wogoman | 436/45 |
| 5,110,552 A | 5/1992 | Guigan | 422/64 |
| 5,122,284 A | 6/1992 | Braynin et al. | 210/782 |
| 5,149,501 A | 9/1992 | Babson et al. | 422/58 |
| 5,160,702 A | 11/1992 | Kopf-Sill et al. | 422/72 |
| 5,171,533 A | 12/1992 | Fine et al. | 422/72 |
| 5,186,844 A | 2/1993 | Burd et al. | 210/782 |
| 5,186,896 A * | 2/1993 | Bouchee et al. | 422/72 |
| 5,192,506 A | 3/1993 | Kureshy et al. | 422/64 |
| 5,207,634 A | 5/1993 | Greenstein | 494/10 |
| 5,242,606 A | 9/1993 | Braynin et al. | 210/787 |
| 5,254,479 A | 10/1993 | Chemelli | 436/180 |
| 5,256,376 A | 10/1993 | Callan et al. | 422/102 |
| 5,290,518 A | 3/1994 | Johnson | 422/58 |
| 5,296,911 A | 3/1994 | Weyrauch et al. | 356/73 |
| 5,304,348 A | 4/1994 | Burd et al. | 422/72 |
| 5,314,825 A | 5/1994 | Weyrauch et al. | 436/43 |
| 5,320,808 A | 6/1994 | Holen et al. | 422/64 |
| 5,376,063 A | 12/1994 | Greenstein | 494/37 |
| 5,403,415 A | 4/1995 | Schembri | 156/73.1 |
| 5,409,665 A | 4/1995 | Burd | 422/64 |
| 5,416,026 A | 5/1995 | Davis | 436/66 |
| 5,427,915 A | 6/1995 | Ribi et al. | 435/7.92 |
| 5,439,645 A | 8/1995 | Saralegui et al. | 422/64 |
| 5,447,440 A | 9/1995 | Davis et al. | 435/6 |
| 5,449,621 A | 9/1995 | Klein | 436/45 |
| 5,457,053 A | 10/1995 | Burd et al. | 436/45 |
| 5,472,603 A | 12/1995 | Schembri | 210/380.1 |
| 5,478,750 A | 12/1995 | Bernstein et al. | 436/164 |
| 5,522,255 A * | 6/1996 | Neel et al. | 73/64.43 |
| 5,525,304 A | 6/1996 | Mattson et al. | 422/104 |
| 5,526,111 A * | 6/1996 | Collins et al. | 356/39 |
| 5,578,269 A | 11/1996 | Yaremko et al. | 422/64 |
| 5,589,399 A | 12/1996 | Allen et al. | 436/169 |
| 5,627,041 A | 5/1997 | Shartle | 435/7.24 |
| 5,639,428 A | 6/1997 | Cottingham | 422/112 |
| 5,646,049 A | 7/1997 | Tayi | 436/518 |
| 5,672,317 A | 9/1997 | Bühler et al. | 422/65 |
| 5,814,279 A | 9/1998 | Biesel et al. | 422/72 |
| 5,916,522 A * | 6/1999 | Boyd et al. | 422/58 |
| 5,919,711 A * | 7/1999 | Boyd et al. | 436/178 |
| 6,002,475 A * | 12/1999 | Boyd et al. | 356/246 |
| 6,124,585 A * | 9/2000 | Riedel et al. | 250/208.1 |

* cited by examiner

CARTRIDGE-BASED ANALYTICAL INSTRUMENT USING CENTRIFUGAL FORCE/PRESSURE FOR METERING/TRANSPORT OF FLUIDS

BACKGROUND OF THE INVENTION

1. Field of the Invention

The present invention relates generally to systems and methods which are used to analyze fluids which may or may not contain solid components. More particularly, the present invention relates to instruments and methods which are used in clinical laboratories and other healthcare locations to analyze blood and other bodily fluids.

2. Description of Related Art

Clinical chemistry involves the qualitative and quantitative analyses of body fluids, such as blood, urine, spinal fluid and other materials. Clinical chemistry encompasses multiple specialty testing areas including coagulation, hematology, immunochemistry, as well as chemistry. The test results derived from such analyses are used by physicians and other healthcare professionals to diagnose, monitor and treat diseases. The analysis protocols, instrumentation and other equipment utilized in clinical laboratory testing must be capable of providing accurate and repeatable test results. In addition, it is desirable that the procedures and instrumentation be simple and efficient. The testing equipment and procedures should be versatile enough that they can be used in healthcare locations where relatively few samples are tested as well as in larger clinical laboratories where the number of samples being tested on a daily basis is quite large.

Another consideration in designing analytical equipment for use by healthcare personnel is the amount of sample available for testing. In many situations, the amount of blood or other bodily fluid available is relatively small. Accordingly, there has been a trend in clinical chemistry to develop analytical systems which are capable of conducting numerous different chemical analyses on relatively small amounts of sample. In general, the goal has been to develop clinical analytical systems which provide the maximum number of medical tests utilizing the minimum amount of sample. In such systems, it is essential that the sample be accurately metered to provide a precise aliquot of sample for testing.

In achieving the above goals, a multitude of different analytical procedures and approaches have been investigated. In one approach, instruments have been developed which have a single sample introduction site. The equipment is designed so that the sample is split, metered and routed to various locations within the system where multiple chemical analyses take place. Other systems do not include internal sample splitting/metering devices and rely on the clinical chemist to separate the sample into small aliquots which are introduced into various instruments which are capable of conducting a maximum of only a few chemical analyses at one time.

There is a continuing need to develop and provide clinical chemistry instruments which are not only accurate, but versatile enough to meet the demands of modern medicine. The instruments should be simple enough to be used by not only highly-skilled laboratory technicians, but also by other healthcare personnel who may only be required to conduct laboratory tests intermittently. The instruments and procedures should be compact and versatile enough so that they can be utilized in clinical laboratories which analyze thousands of samples daily, while at the same time being adaptable to doctors' offices, home healthcare agencies and nursing homes where the number of tests being conducted is not as great. In addition, the instruments should be versatile enough to be useful in conducting a wide variety of blood analyses which are presently being routinely utilized. The instruments should also be adaptable to conducting blood or other bodily fluid tests which will be developed in the future.

SUMMARY OF THE INVENTION

In accordance with the present invention, an analytical instrument is provided which is compact and versatile. The instrument is a "cartridge-based" instrument in that it is designed to receive and process individual self-contained cartridges which are pre-loaded with sample and any required reagents. The instrument also utilizes centrifugal force and pressure to meter and transport sample and reagents within the cartridge during the analysis process. The instrument is capable of simultaneously analyzing multiple test cartridges. The multiple test cartridges may be set up to conduct the same or different analytical tests. The instrument is extremely versatile because the cartridges are designed to carry out a wide variety of test protocols.

The instrument includes a cartridge carousel assembly which receives the analytical cartridges. The cartridges are self-contained units which incorporate a sample metering/separation system which is operated by centrifugal force. The cartridge also includes a sample transport system which is operated by externally-applied pressure wherein the sample is transferred to a test element which provides a detectable analytical property of the fluid sample. The cartridge carousel is composed of a cartridge rotor plate which includes a center and a plurality of cartridge ports which are located in spaced relation radially outward from the center of the plate. The cartridge ports are shaped to receive and hold the cartridges during testing procedures. The cartridge carousel assembly further includes a rotary drive mechanism which rotates the cartridge rotor plate about the center thereof. It is this rotation of the cartridge rotor plate which activates the metering/separation system of the cartridge.

The analytical instrument further includes a sample transport actuator which is designed to activate the pressure-operated sample transport system of the cartridge either before or after the sample metering/separation system has been actuated by rotation of the cartridge rotor plate. The instrument also includes a detector which measures one or more detectable analytical properties of the fluid sample which are provided by the test element of the cartridge as part of the analytical process.

As a further feature of the present invention, the analytical instrument includes a tracking and control unit which tracks and controls the rotary drive mechanism and sample transport actuator to provide coordinated operation of the centrifugal force operated sample metering/separation system and pressure operated sample transport system. This coordinated operation provides delivery of a metered amount of sample fluid to the test element of the cartridge. The tracking and control unit includes a user input interface for receiving data input from the operator of the instrument as well as a central processing unit, a real time processor and a data output interface which provides output of results of the measurements made by the detector.

The analytical instrument in accordance with the present invention is well-suited for conducting a wide variety of clinical tests. The versatility of the instrument is only limited by the different types of test cartridges. The instrument is compact and simple to use. Accordingly, it can be used in a wide variety of settings ranging from large clinical laboratories which conduct thousands of tests daily to small hospital laboratories or doctors offices.

The above discussed features and attendant advantages of the present invention will become better understood by reference to the following detailed description when taken in conjunction with the accompanying drawings.

DETAILED DESCRIPTION OF THE INVENTION

Figure 1:
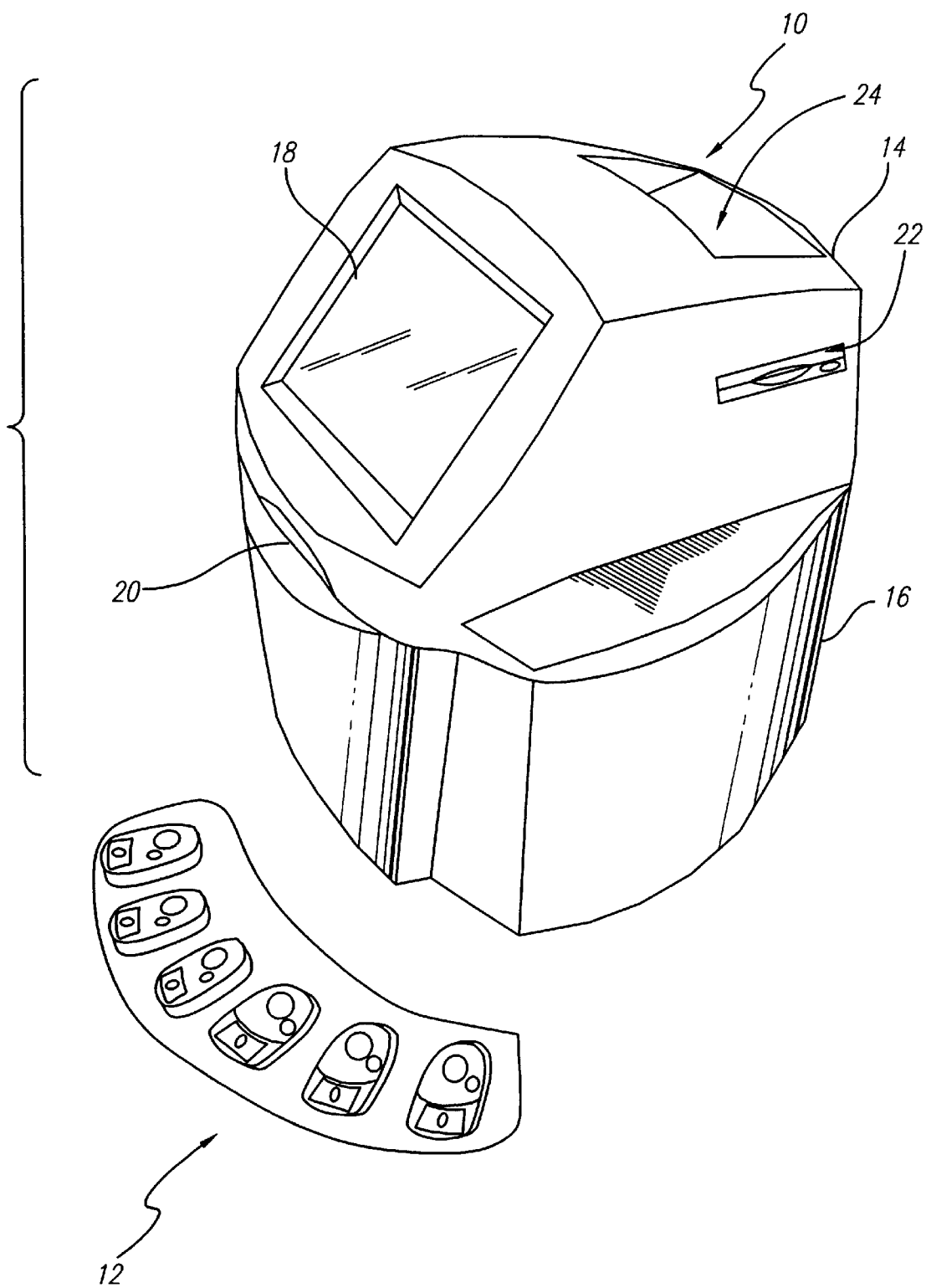
FIG. 1 is a perspective view of a preferred exemplary analytical instrument in accordance with the present invention showing the outer housing thereof. Also shown in FIG. 1 are analytical cartridges which are designed to be processed by the instrument.

A preferred exemplary analytical instrument in accordance with the present invention is shown generally at 10 in FIG. 1. The outer housing of the instrument is shown in more detail in U.S. Pat. No. Design. 424,1956 The instrument is designed to receive and process self-contained analytical cartridges such as those shown generally at 12. The cartridges 12 include test elements which utilize reflectance, transmittance or electrochemistry. The transmittance type analytical cartridge is shown in FIGS. 8–10 and 12. This type of cartridge is also described in detail in international application No. PCT/US98/15616. This type of cartridge will also be described briefly below.

Figure 11:
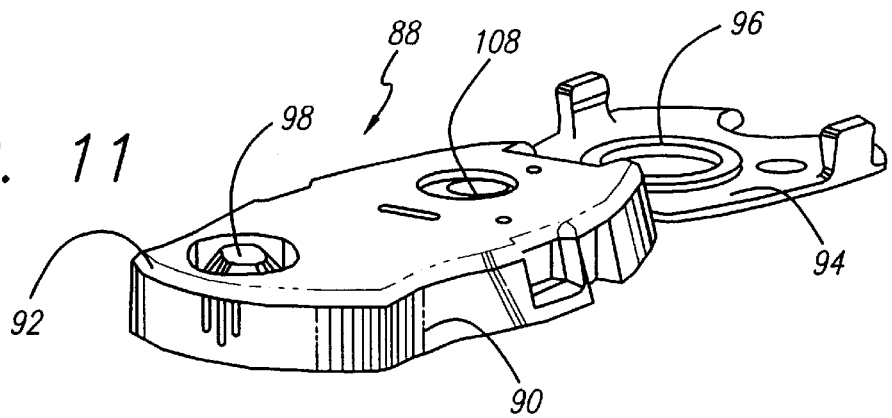
FIG. 11 is a perspective view of a preferred exemplary test cartridge which includes a pressure-operated reagent transport system and an electrochemical test element.
Figure 13:
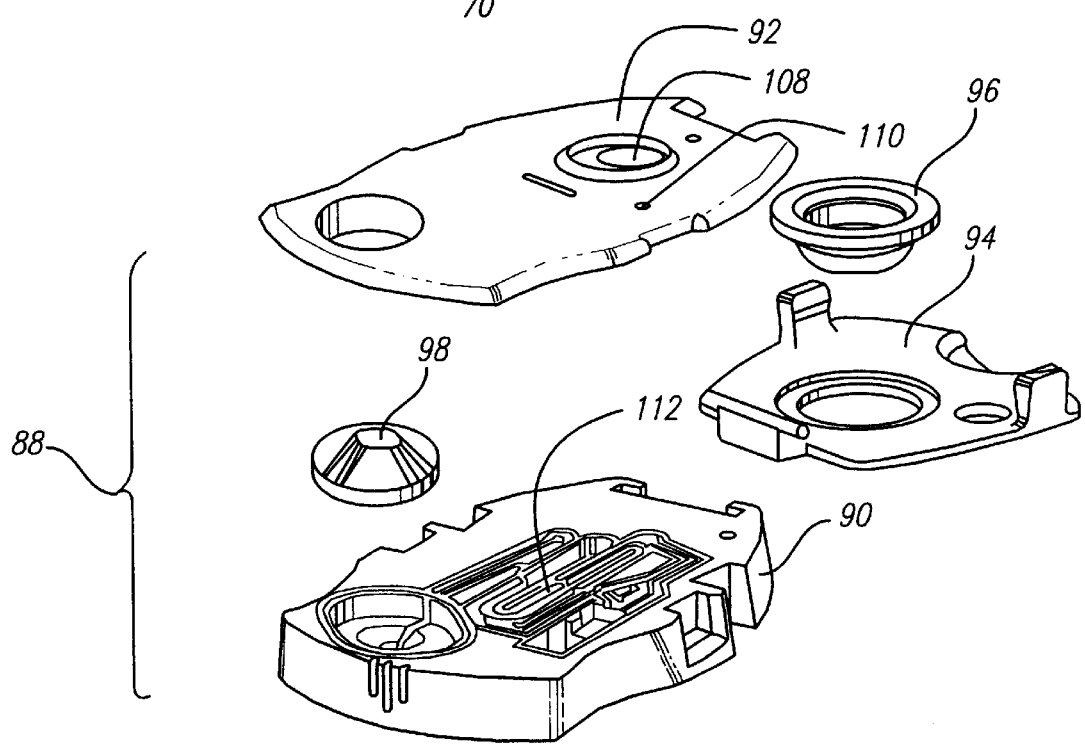
FIG. 13 is an exploded view of the electrochemical cartridge shown in FIG. 11.
Figure 14:
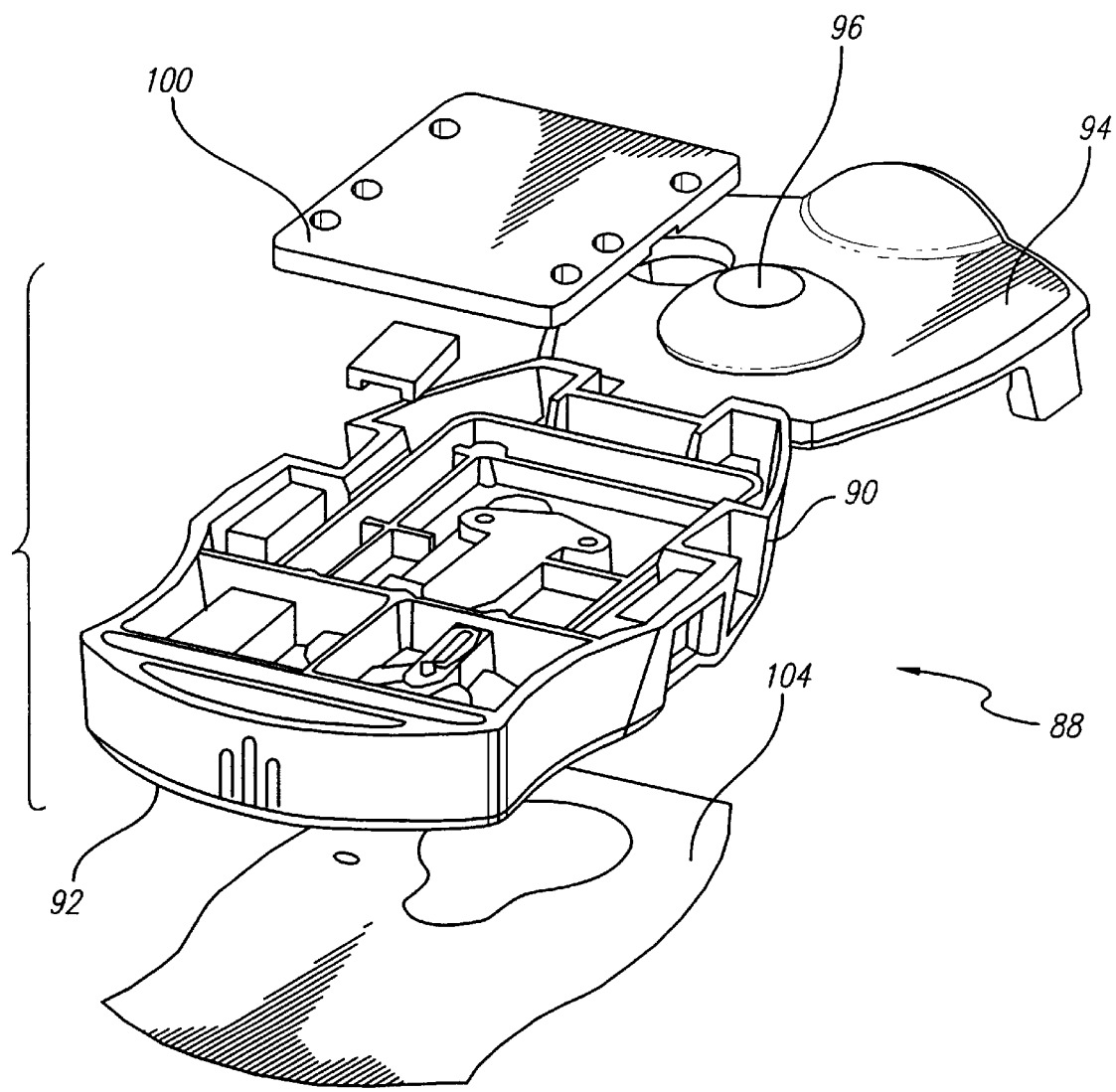
FIG. 14 is an exploded view of the electrochemical cartridge of FIG. 11 showing the electrochemical test element.
Figure 15:
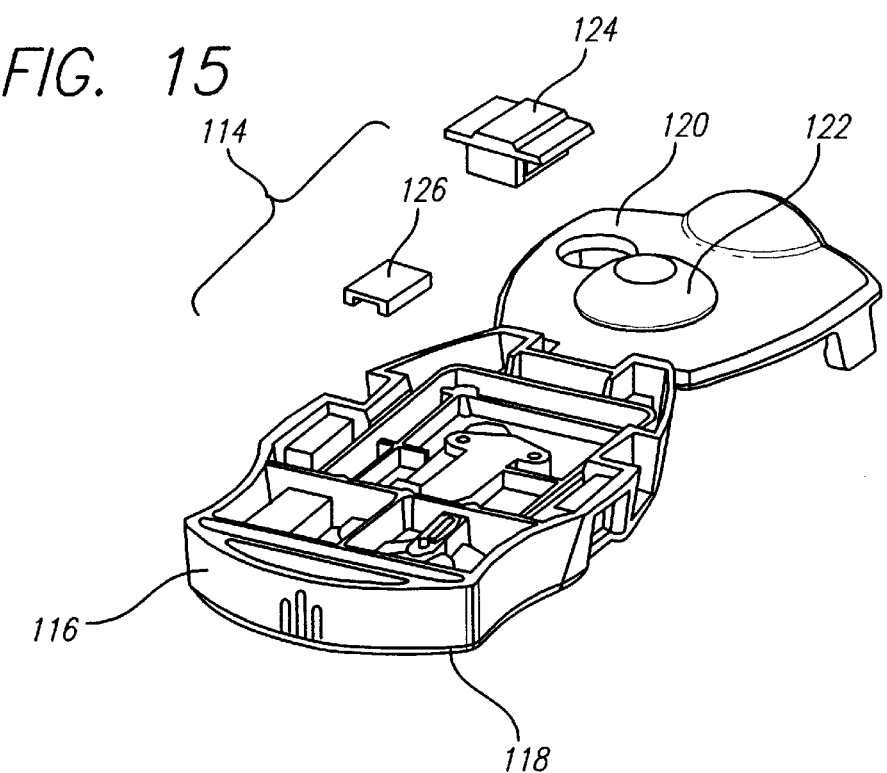
FIG. 15 is a partially exploded view of an analytical cartridge in accordance with the present invention which includes a cuvette test element which allows transmittance-based detection by the analytical instrument.
Figure 16:
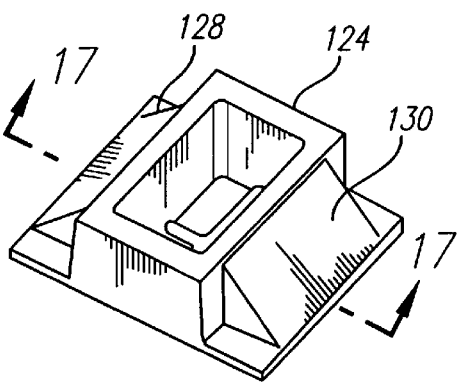
FIG. 16 is a detailed view of the cuvette which forms part of the transmittance analytical test cartridge shown in FIG. 15.
Figure 17:
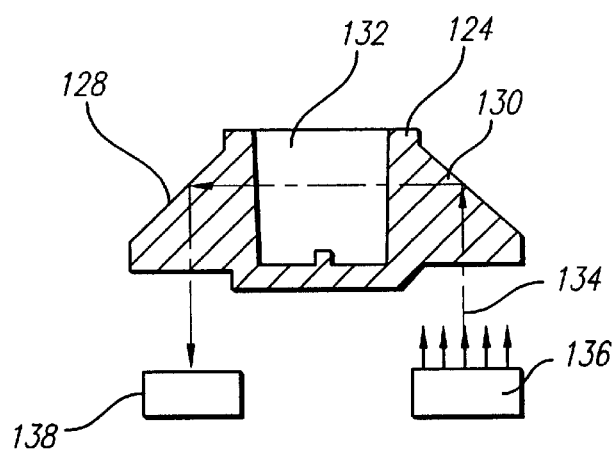
FIG. 17 is a sectional view of FIG. 16 which depicts the pathway of light through the cuvette detector.

The type of analytical cartridge which utilizes an electrochemical test element is shown in FIGS. 11, 13 and 14. Such electrochemical test cartridges are also described in International patent application No. PCT/US99/0628. The electrochemical cartridge will also be briefly described below. The transmittance type analytical cartridge is shown in FIGS. 15–17. This type of cartridge is also described in detail in International patent application No. PCT/US99/01707.

The detailed descriptions of the three types of analytical cartridges set forth in the above three pending applications are hereby incorporated by reference. The brief description of these cartridges set forth later on in the body of this specification is provided to show how a preferred exemplary embodiment of the present analytical instrument operates. It will be understood by those skilled in the art that the analytical instrument of the present invention may be utilized for analyzing other analytical cartridges which have similar properties to the preferred exemplary cartridges described herein and set forth in the above-referenced patent applications.

Referring again to FIG. 1, the analyzer 10 includes an upper housing cover 14 and a lower housing cover 16. A computer input/output pad or screen 18 is located in the upper cover 14 to allow the operator of the instrument to view information and input. The housing cover 14 further includes an inlet port 20 through which the cartridges 12 are inserted into the instrument. A central processing unit is located within the upper housing cover 14. A disc inlet 22 is provided for allowing the operator to insert floppy disks into the central processing unit to provide software updates as well as transport other data and information into and out of the central processing unit. The upper housing cover 14 also includes a port and shelf 24 where a paper copy of report results and other data is made available to the operator.

Figure 2:
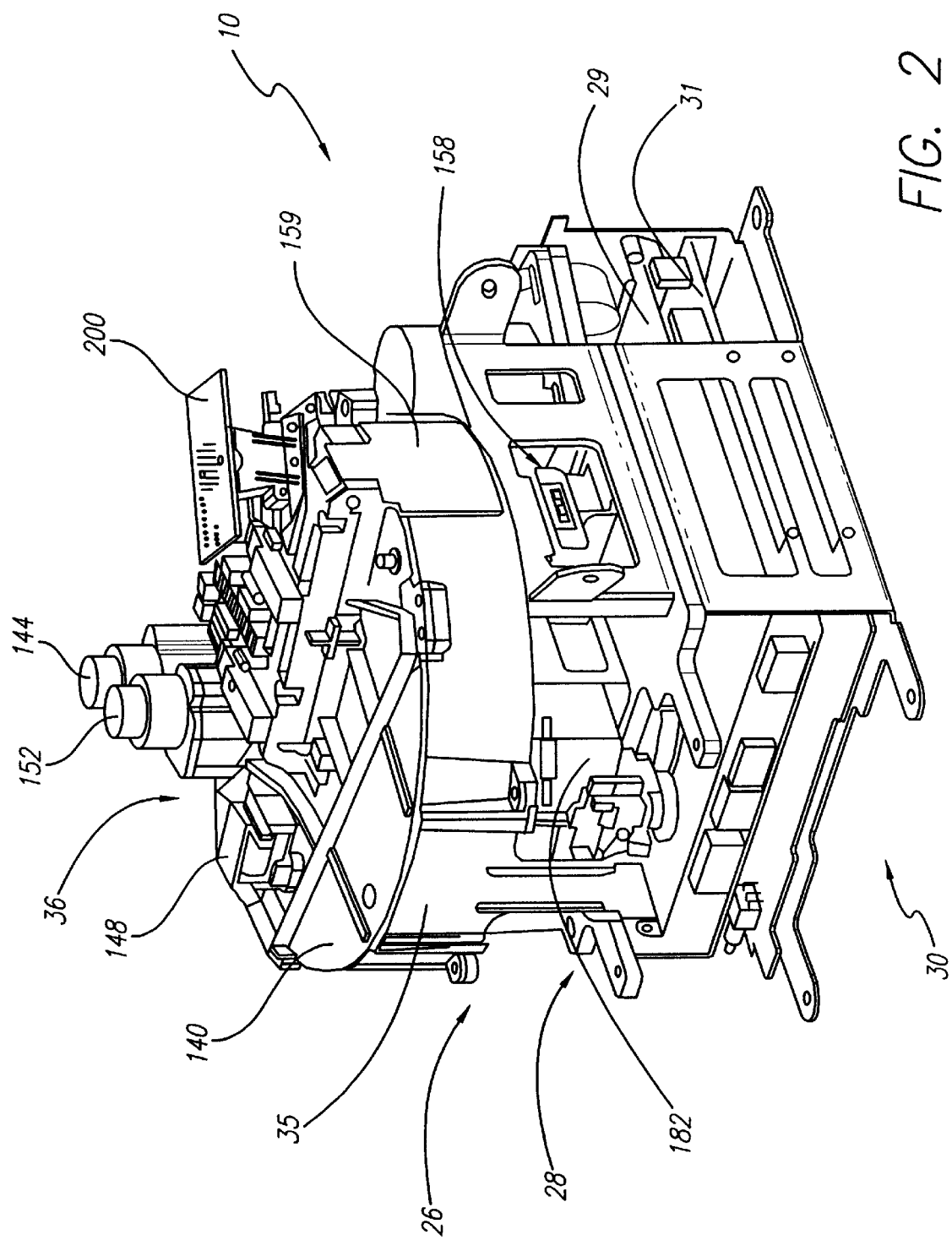
FIG. 2 is a perspective view of an analytical instrument in accordance with the present invention wherein the housing cover and user interface has been removed.
Figure 3:
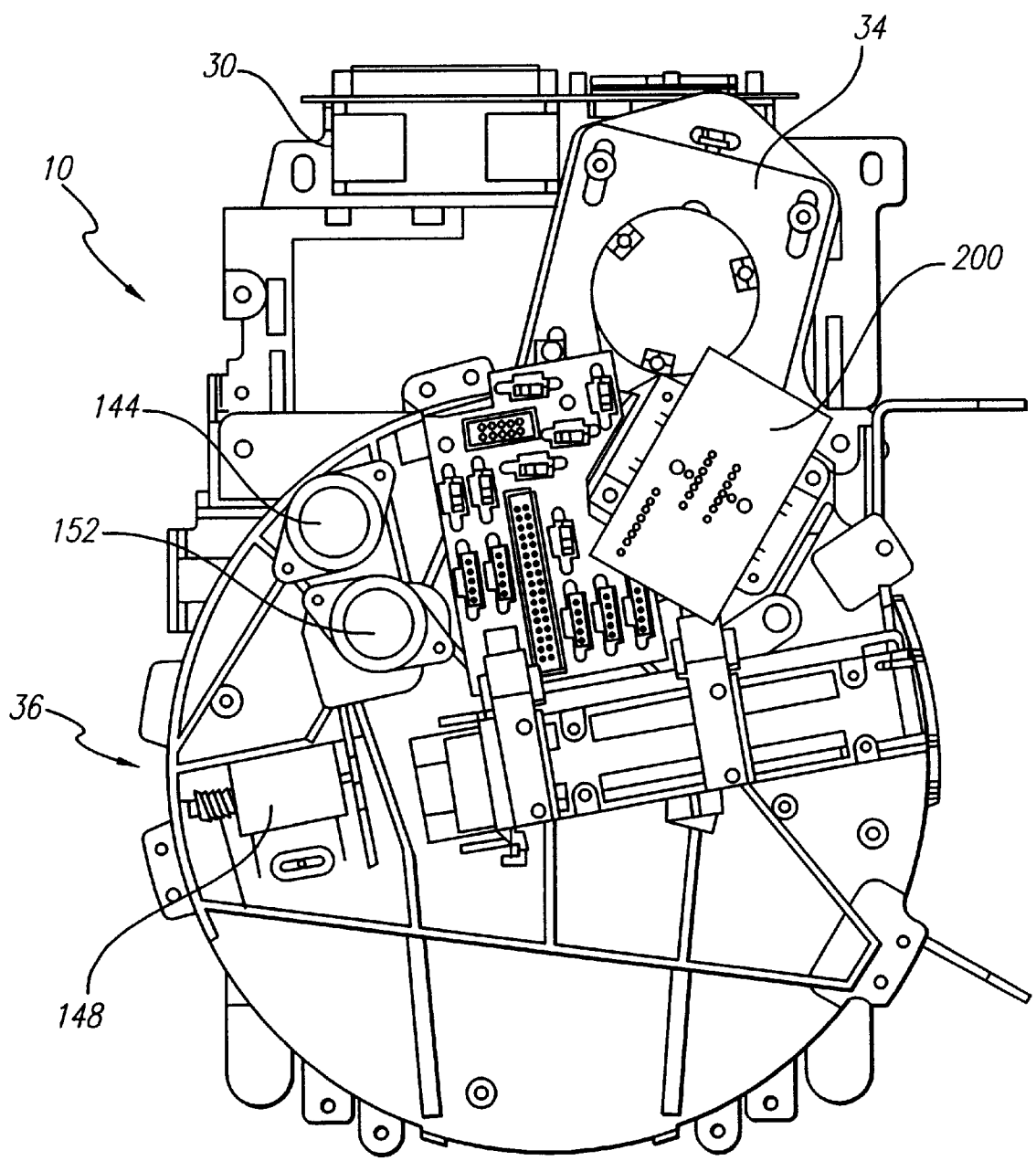
FIG. 3 is a top view of the preferred exemplary analytical instrument shown in FIG. 2.
Figure 4:
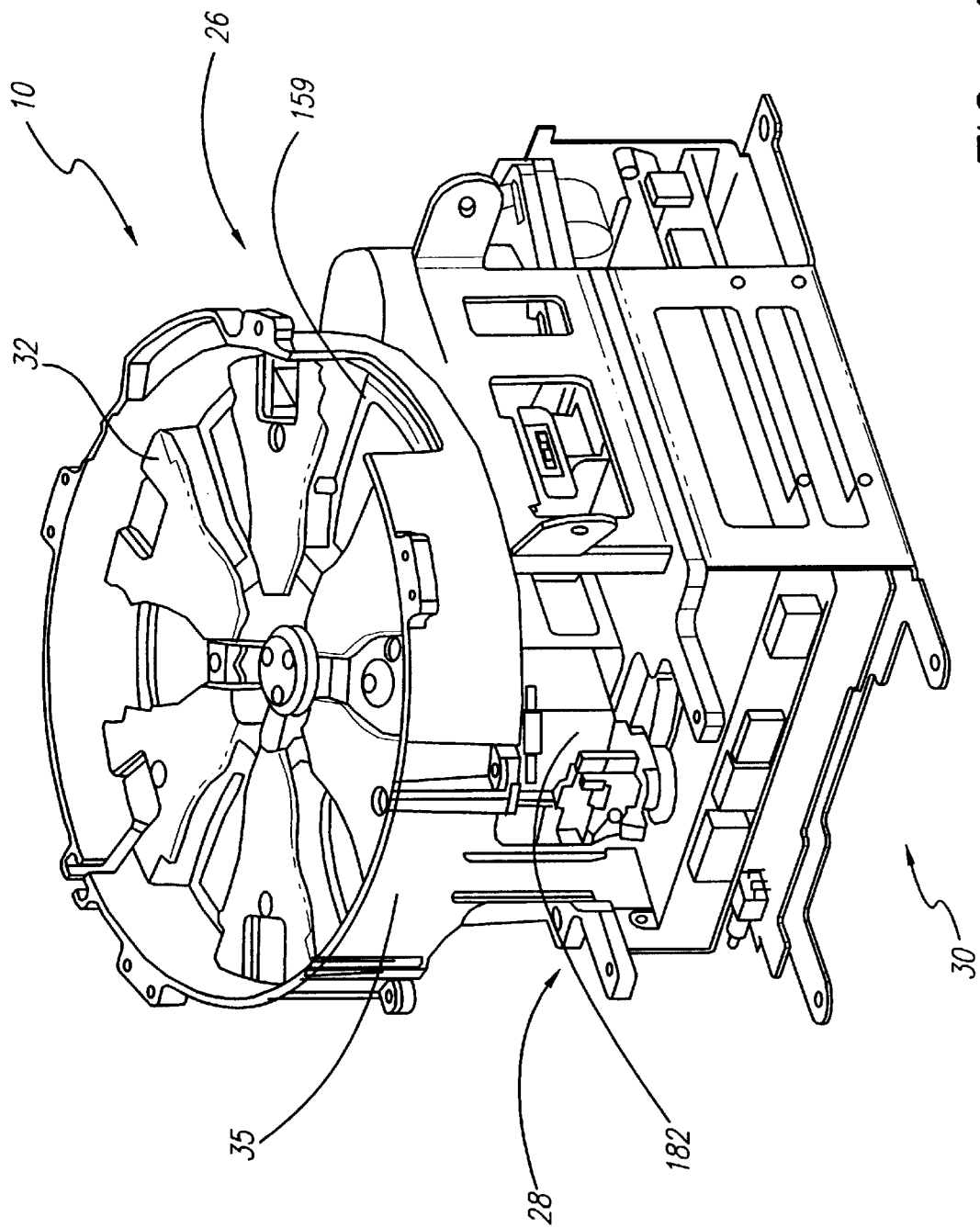
FIG. 4 is a perspective view of the preferred exemplary instrument in which the top portion has been removed to expose the cartridge rotor plate.

The analyzer is shown in FIGS. 2–4 with the housing covers and central processing unit removed. The instrument includes a cartridge carousel assembly shown generally at 26, a detector assembly located below the cartridge carousel assembly 26 and shown generally at 28 and a tracking and control unit which is located in the bottom of the instrument and is shown generally at 30. The tracking and control system 30 includes two circuit boards 29 and 31 which are connected to the central processing unit and a real-time processor to provide overall tracking and control functions for the instrument.

Figure 5:
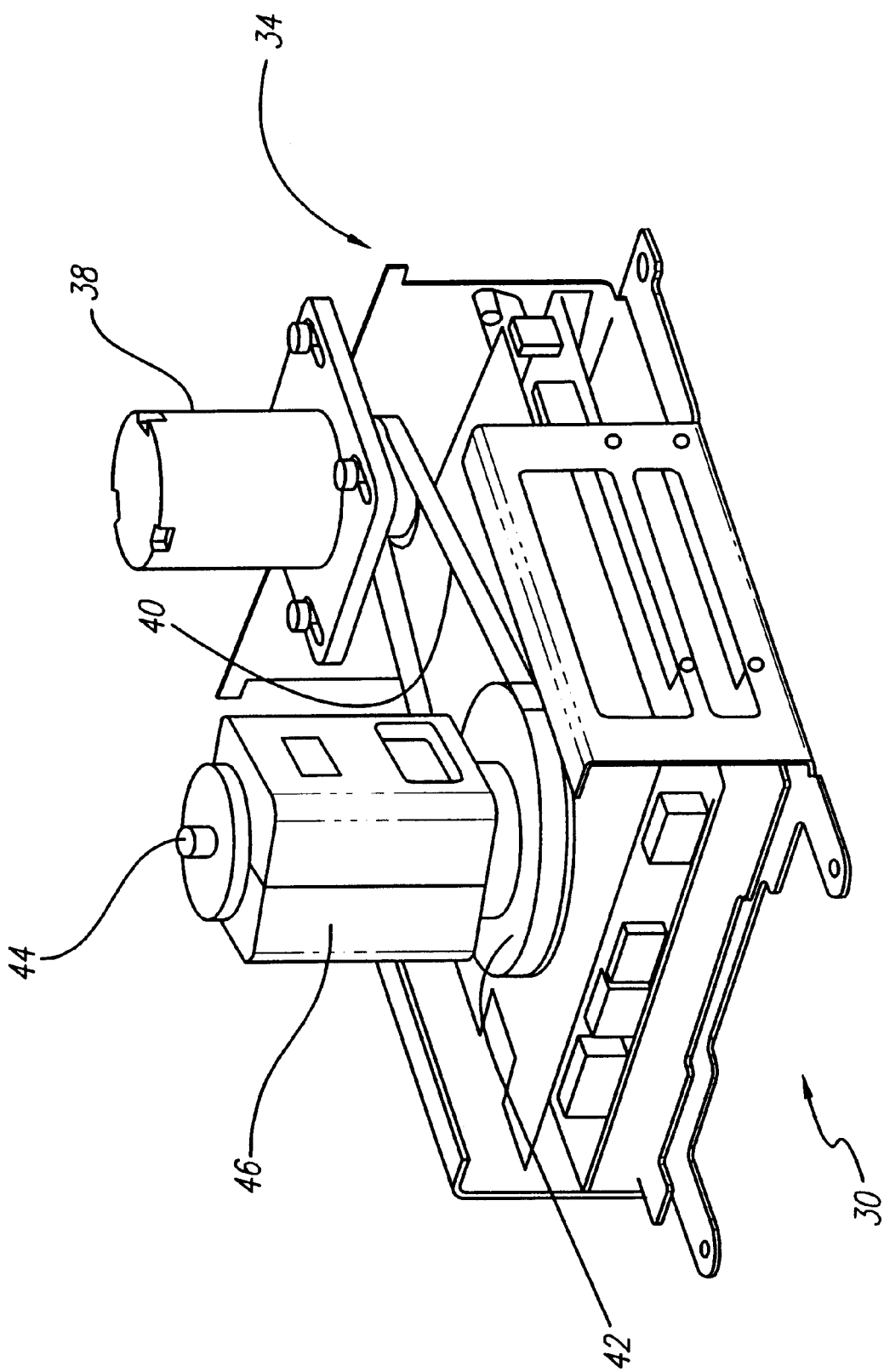
FIG. 5 is a view of the rotary drive mechanism and real time processing unit which is located at the bottom of the instrument as shown in FIGS. 2–4.

The cartridge carousel assembly includes a cartridge rotor plate 32, a rotary drive mechanism 34 and sample/reagent actuators 36. A retractable door 35 is provided which can be lowered to allow cartridges 12 to be introduced into the rotor plate 32. As shown in FIG. 5, the rotary drive mechanism 34 includes a motor and pulley assembly 38 which drives belt 40 and pulley 42 which is connected to driveshaft 44. The cartridge rotor plate 32 is connected to the driveshaft 44. An encoding assembly 46 is provided to track the position of the cartridge rotor plate 32 and provide outputs which are part of the tracking and control system which operate motor 38 to provide controlled stopping and rotation of cartridge rotor plate 32 at various times and at various speeds.

Figure 6:
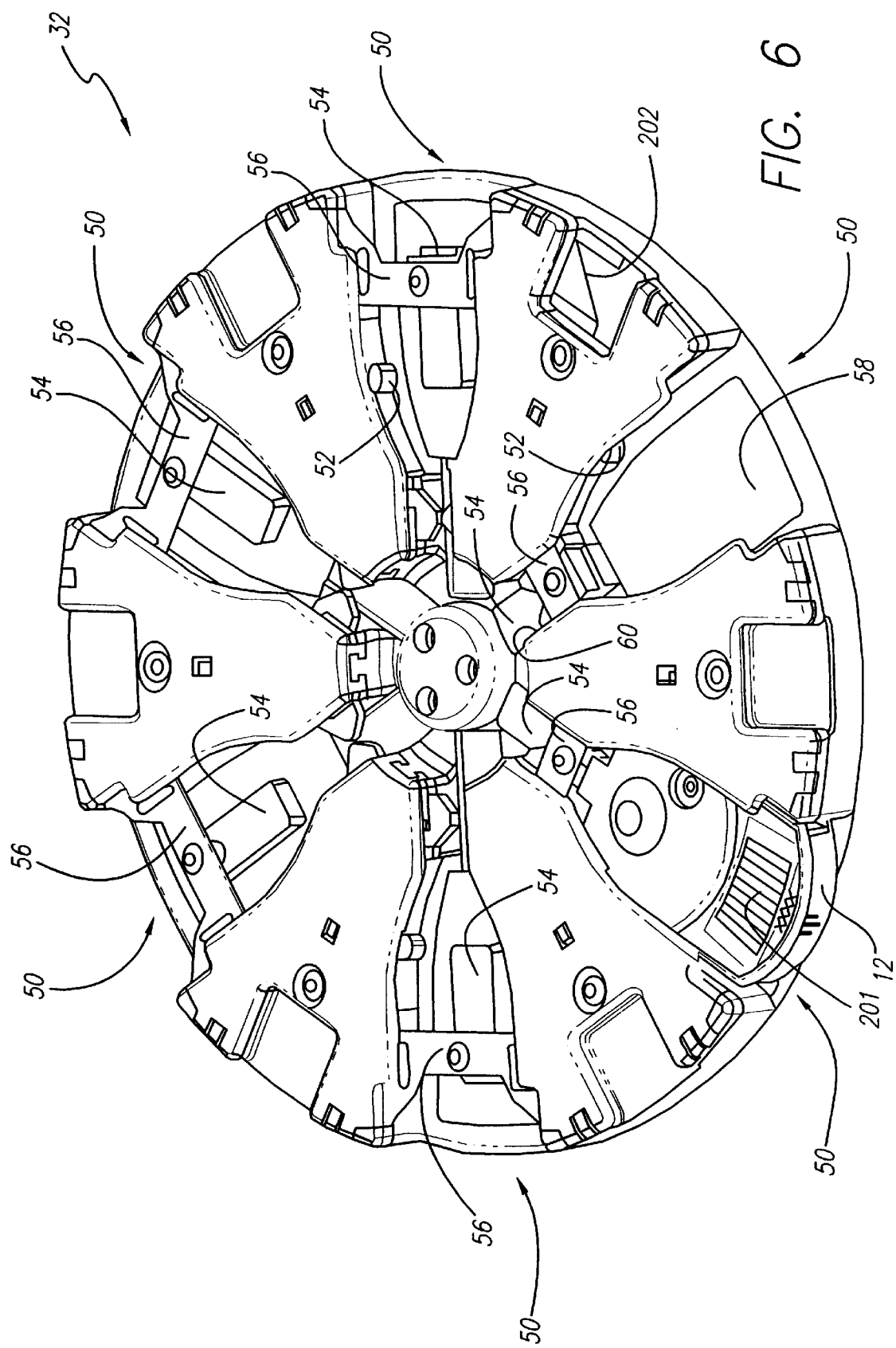
FIG. 6 is a detailed view of the cartridge rotor plate.
Figure 7:
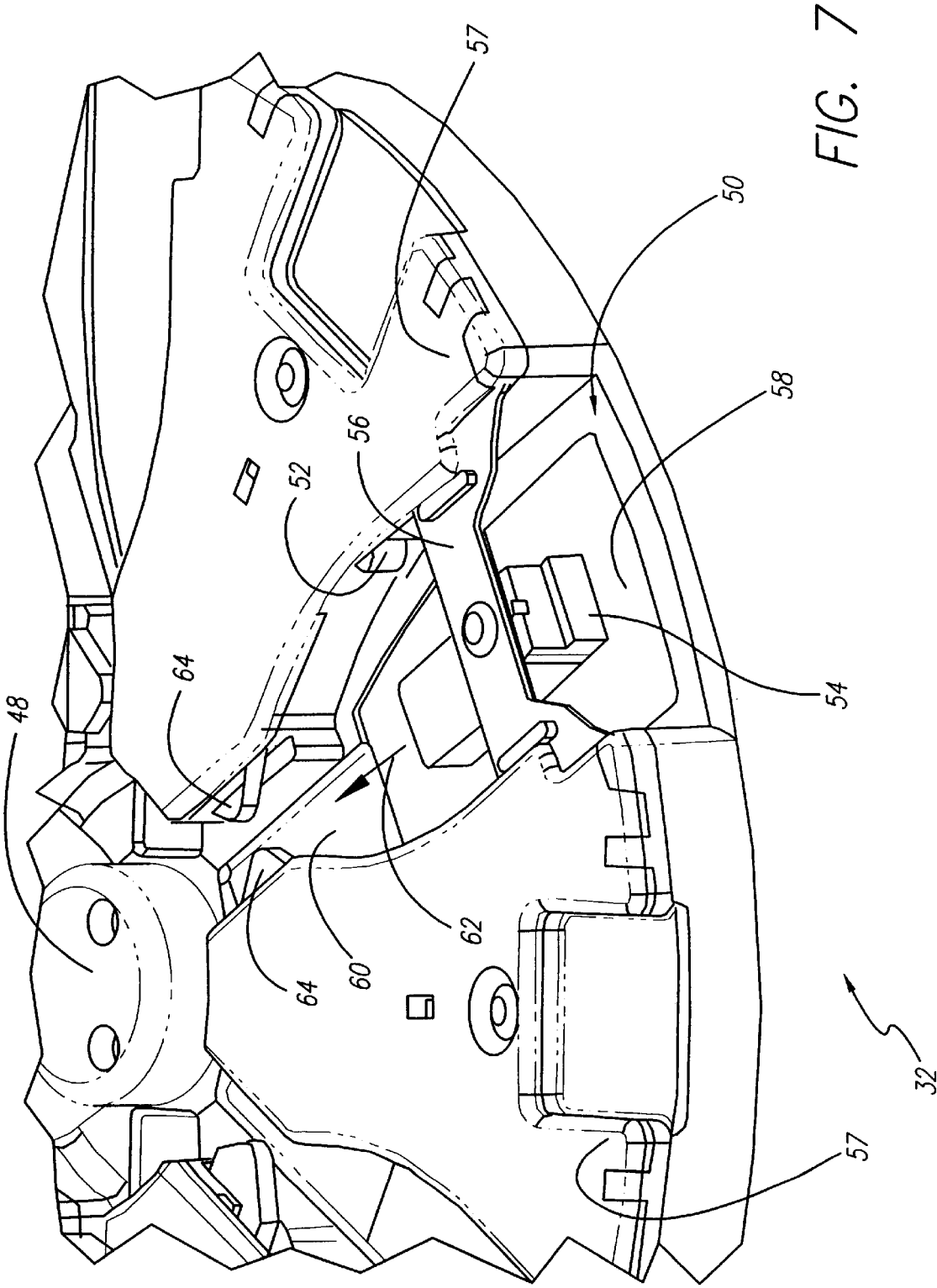
FIG. 7 is a detailed view of the cartridge rotor plate which shows the locking mechanism which holds the cartridge in place during rotation of the cartridge plate as well as the balancing mechanism which ensures that the rotor plate is balanced to ensure non-asymmetric rotation.
Figure 8:
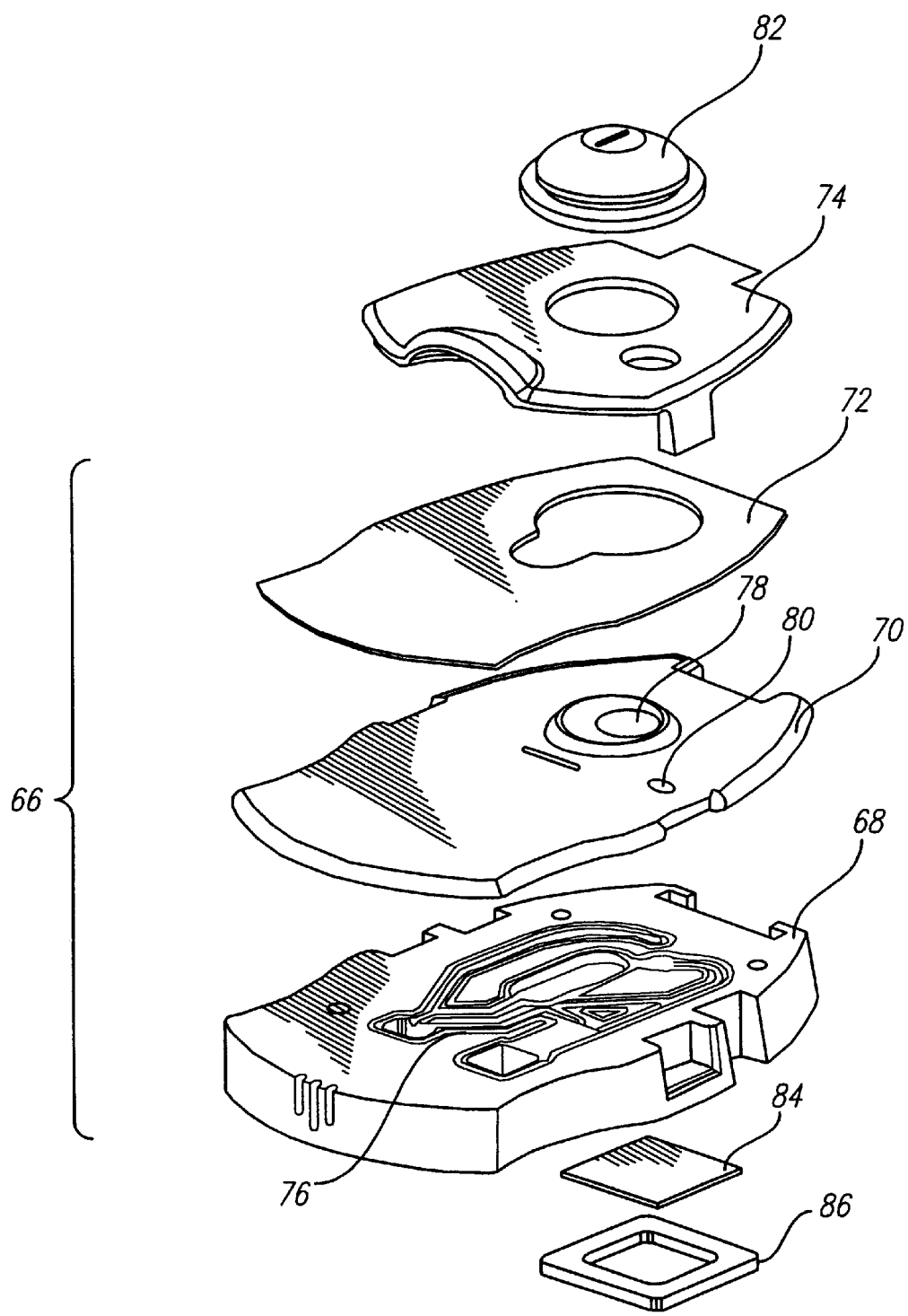
FIG. 8 is an exploded view of a preferred exemplary analytical cartridge which includes a test element which is designed to be used with a reflectance detector system.
Figure 9:
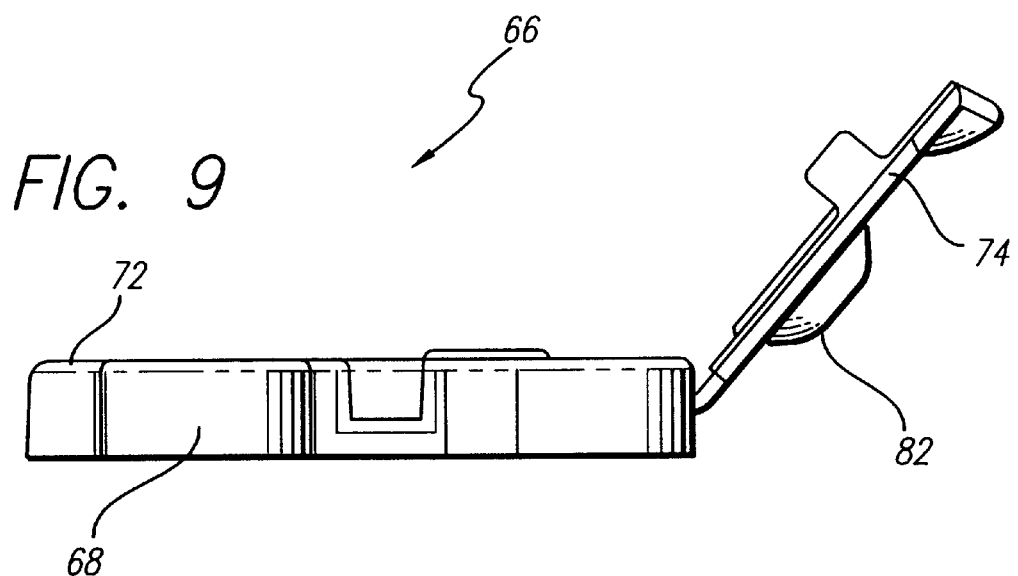
FIG. 9 is a side view of the reflectance test cartridge shown in FIG. 8.
Figure 10:
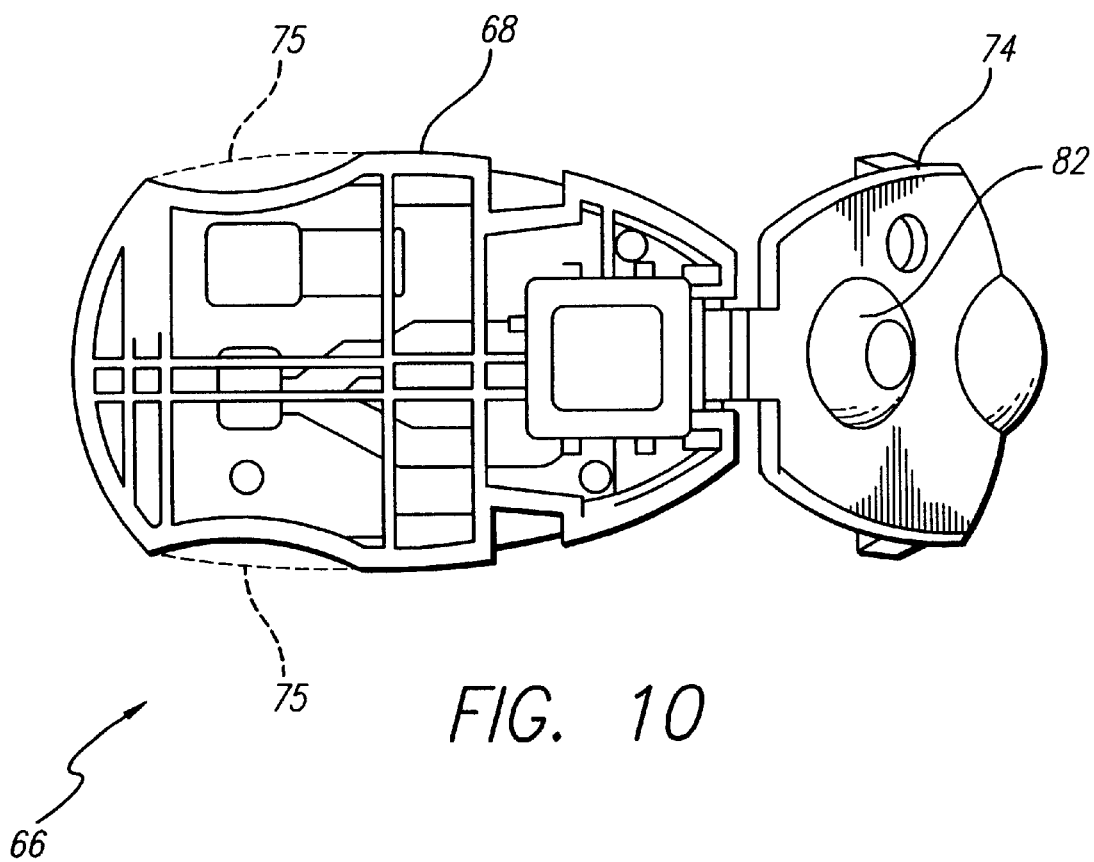
FIG. 10 is a bottom view of the reflectance cartridge shown in FIG. 8.
Figure 31:
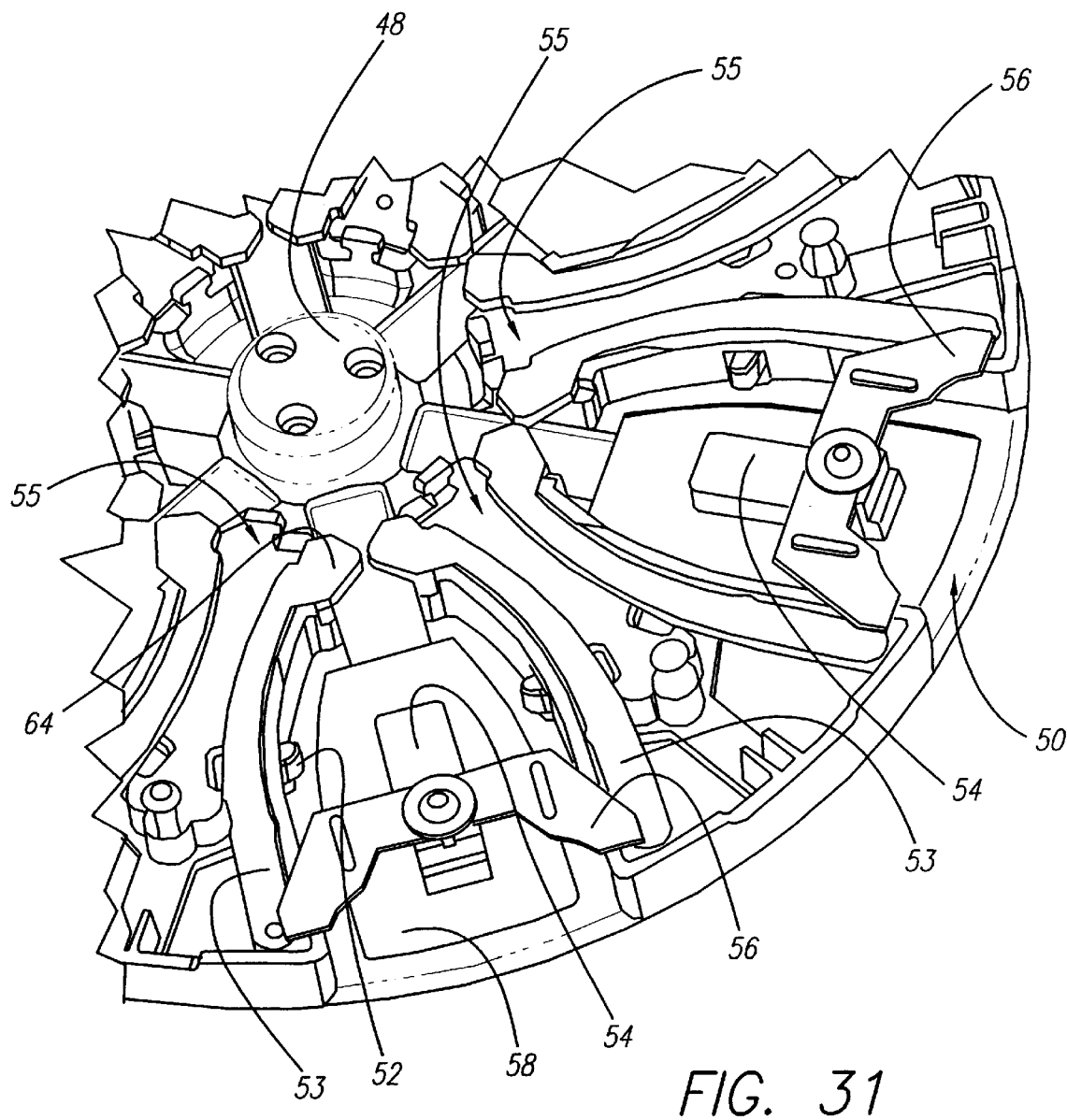
FIG. 31 is a perspective view of the cartridge rotor plate wherein the platter caps have been removed to show the cartridge latching mechanism.

The cartridge rotor plate 32, as best shown in FIGS. 6, 7 and 31, includes a center 48 and a plurality of cartridge ports 50 which are located in spaced relation radially outward from the center 48. The cartridge ports 50 are shaped to receive the analytical cartridges which are shown in FIGS. 8–17. An exemplary cartridge 12 is shown in position within the cartridge rotor plate 32 (see FIG. 6). The rotor plate 32 includes locking tabs 52 which are located on either side of port 50. The locking tabs 52 engage the sides of cartridge 12 to lock it in place during centrifugation of the cartridges. The rotor plate 32 further includes balance weights 54 which are connected to a support yoke 56.

The cartridge ports 50 are divided into two sections. An outer cartridge dock 58 and an inner balance weight dock 60. When the cartridge 12 is inserted into the cartridge dock 58, as shown in FIG. 6, the balance weight 54 and yoke assembly 56 are pushed via a yoke mounting track into the balance weight dock 60. The movement of the balancing weight 54 and yoke 56 from the cartridge dock 58 into the balance weight dock 60 is represented by arrow 62 in FIG. 7. The yoke 56 is held in place and guided by top plates 57. In FIG. 31, the rotor plate 32 is shown with the top plates 57 being removed.

As the cartridge 12 is moved into dock 58, it contacts tabs 52 and pushes the tabs 52 outward. The tabs 52 are connected to arms 53. The arms 53 include inner tabs 64 which are spring-biased inward by springs located between the arms at 55 in FIG. 31. The springs are not shown. Once the cartridge 12 reaches its final location in dock 58, the tabs are spring-biased into locking engagement with indentations in the cartridge 12. The inner tabs 64 are located so that they do not interfere with movement of the weight 54 into the balance weight dock 60.

If a cartridge 12 is not inserted into dock 58, the balance weight 54 and yoke 56 remain within the cartridge dock 58 during rotation of plate 32. This provides balancing of the plate 32 to substantially reduce vibration and prevent possible damage which might occur during high-speed rotation of an unbalanced plate. This counterbalance system allows the operator to insert as few as one cartridge into the instrument for analysis or as many as six. An even larger number of cartridges can be inserted into the cartridge rotor plate if the number of ports is increased. Referring to FIG. 6, the balance weight located in the port 50 which is adjacent to the cartridge 12 (counterclockwise) is shown located within the balance weight dock 60. Upon initial rotation, this particular counterweight will slide outward into the cartridge dock 58 to provide balancing of the plate 32.

As mentioned above, the cartridges 12 which are processed by the analytical instrument of the present invention can be of at least three types. The first type is shown at 66 in FIGS. 8–10 and 12. The cartridge 66 includes a body 68, top plate 70, label 72 and cover 74. The concave curve in the cartridge body sides may be eliminated as shown in phantom at 75 in FIG. 10, if desired. The cartridge includes a sample metering/separation system which is shown at 76 in FIG. 8. The sample is introduced into the system 76 through sample introduction portion 78. The system also includes a vent port 80 which is required for proper operation of the system.

The system 76 is designed to meter out an accurate sample aliquot when the cartridge is subjected to centrifugation. In addition, the system 76 is designed to provide separation of solid components, such as blood cells, from the sample during centrifugation, if desired. The cartridge 66 also includes a flexible septum 82 which forms an essential part of the cartridge's pressure-operated sample transport system. As will be described in more detail below, the analytical instrument of the present invention includes a sample transport actuator which compresses septum 82 in order to pressurize the system 76 and transport the previously-metered sample to the test element. The two basic steps of the analytical process are centrifugation of the cartridge to achieve metering and separation of the sample followed by pressurization of system via septum 82 to transport the sample to the test element.

The test element for cartridge 66 is reflectance reagent plate 84 which is held in place within the cartridge by retainer 86. Pressurization of septum 82 transports the sample through system 76 into contact with the reagent plate 84. The result is a detectable analytical property. This analytical property is measured by the analytical instrument, as will be described in more detail below, by focusing radiation of a selected wavelength onto plate 84 and measuring the amount of radiation which is reflected back to a detector. Both the radiation source and reflectance detector are located below the cartridge rotor plate 32.

A second type of analytical cartridge is shown at 88 in FIGS. 11, 13 and 14. Cartridge 88 is similar to cartridge 66 in that it requires centrifugation followed by pressurization in order to carry out analysis of a given sample. The principal differences are that the cartridge 88 includes a system for transporting reagent to the test element and, instead of using a reflectance test element, cartridge 88 utilizes an electrochemical measuring device.

The electrochemical analytical cartridge 88 includes a body 90, top plate 92, cover 94 and flexible septum 96. The cartridge 88 also includes a flexible reagent pouch 98 which is compressed and punctured by a reagent transport actuator to transport reagent to the electrochemical detector which is shown at 100 in FIG. 14. Like cartridge 66, cartridge 88 also includes a label 104. Both labels 104 on cartridge 88 and label 72 on cartridge 66 preferably include a bar code which is shown at 106 in FIG. 12. This bar code is read by the instrument to provide input of data which is specific to the particular cartridge. This information is used by the tracking and control system of the analytical instrument to coordinate the rotary drive mechanism for the cartridge rotor plate and the actuators which operate against the flexible septums and flexible reagent pouches.

The electrochemical cartridge 88 also includes a sample inlet port 108 and vent port 110. The sample metering and transport system is shown at 112 in FIG. 13. This system typically does not include the plumbing required for separation of solid components from the sample because, in general, electrochemical tests do not require separation of solids from the sample. However, the system shown at 112 may be modified to provide sample separation, if desired.

Figure 12:
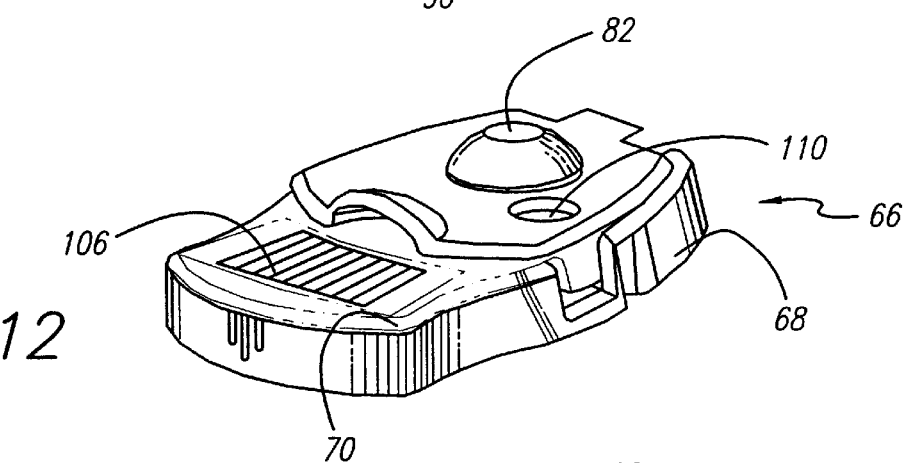
FIG. 12 is a view of the cartridge shown in FIG. 8 showing a bar code reading strip which is used by the instrument to provide tracking and control of cartridge processing.

The cartridge cover 94 is opened in order to allow the operator to place a sample into the cartridge through port 108. The cover is then closed as shown in FIG. 12 and the cartridge inserted into one of the ports 50 in cartridge rotor plate 32. The cartridge is then centrifuged at sufficient speeds and for a sufficient time to meter out an accurate amount of sample within system 112. Septum 82 is then actuated to transport sample liquid to the electrochemical detector 100. In addition, flexible reagent pouch 92 is also compressed. Compression of flexible pouch 98 causes the pouch to be punctured and reagent to be transported to the electrochemical detector 100. The instrument includes an electrochemical detector probes, which will be described in further detail below. The probes contact the electrochemical detector 100 to measure the results of electrochemical testing.

A third type of exemplary cartridge which is processed by the analytical instrument of the present invention is shown in FIGS. 15–17. This type of cartridge is a transmittance-type analytical cartridge which is shown at 114 in FIG. 15. The transmittance cartridge 114 includes a cartridge body 116, top plate 118, cover 120 and septum 122. The transmittance cartridge 114 further includes a cuvette 124 which is held in place by retainer 126. The cuvette 124 is a test element which is capable of being exposed to spectral radiation in order to provide spectrophotometric test results. The cuvette 124 is shown in more detail in FIGS. 16 and 17.

The cuvette 124 includes optical wings 128 and 130 which direct spectral radiation through the cuvette test zone or cell 132 as shown by phantom line 134 in FIG. 17. As will be described in detail below, the analytical instrument of the present invention includes a detector system which has a spectral radiation source shown schematically at 136 in FIG. 17 which is located below the cartridge rotor plate 32. The spectral radiation source directs a focused beam of radiation 134 up to wing 130 which in turn directs the beam through the cuvette test zone or test cell 132 to wing 128 and back down to a detector shown schematically in FIG. 17 at 138.

The internal operation of the three types of cartridges have only been briefly described above in order to provide an understanding of the operation of the analytical instrument 10. A more detailed description of the three types of cartridges can be found in the above-referenced International patent applications.

Figure 18:
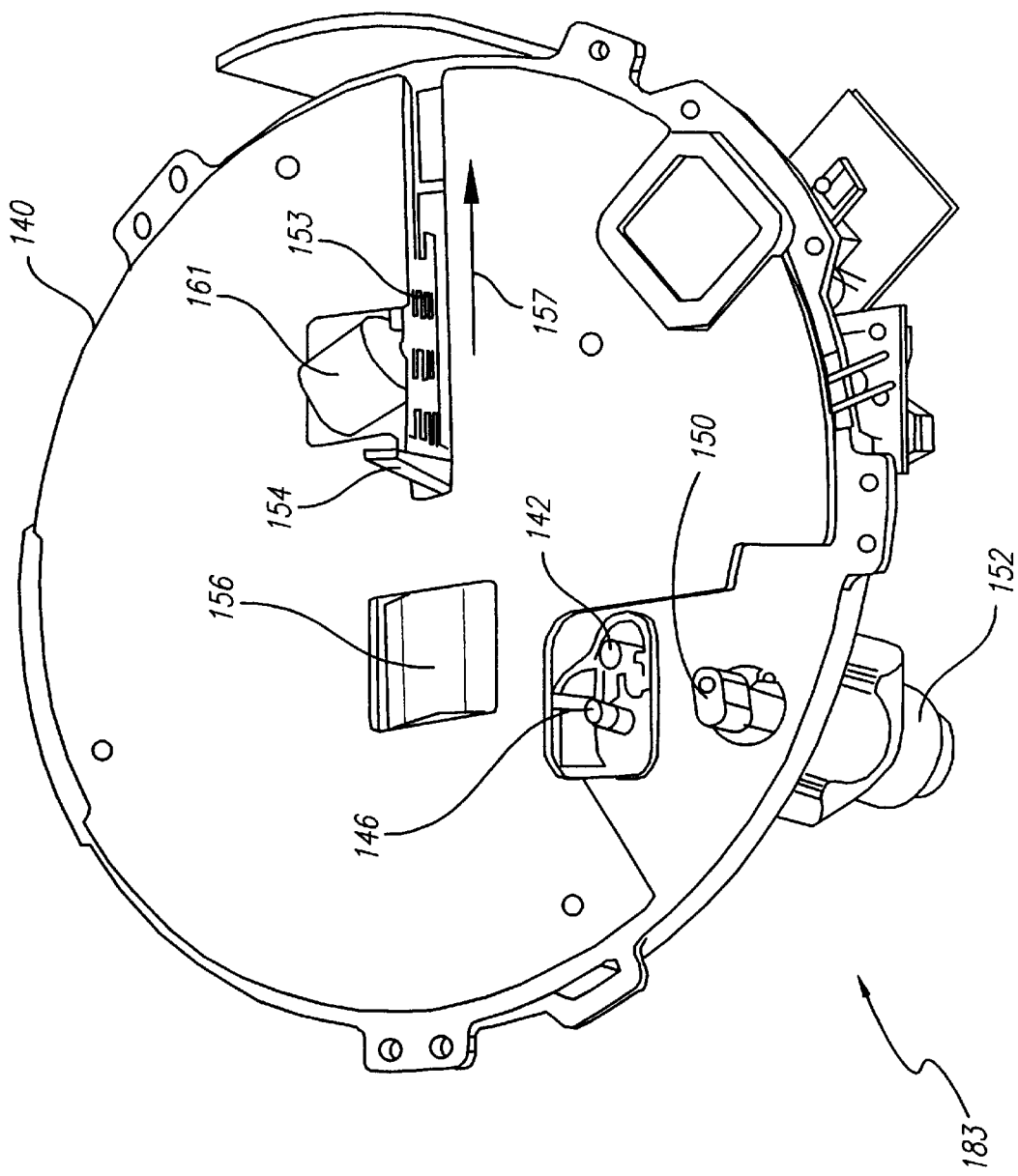
FIG. 18 is a bottom view of the upper housing plate which is located on top of the cartridge rotor plate. This figure depicts a septum actuator, vent seal element and actuator mechanism which form part of the sample transport system which contact the cartridges during processing by the instrument. The figure also depicts the actuator mechanisms which actuate the reagent transport system in the cartridge.

A bottom view of the upper portion 140 of the cartridge carousel assembly 26 is shown in FIG. 18. The upper portion 140 is also shown in place on instrument 10 in FIG. 2. A sample transport actuator is shown at 144 in FIG. 2 and 141 in FIG. 26. Referring to FIGS. 18 and 26–28, actuator 141 includes a septum actuator rod 142 is provided which is movable into contact with the flexible septums on the analytical cartridges to move the septums from a relaxed position to one or more compressed positions to provide transport of metered and/or separated samples to the cartridge test element. A vent seal rod 146 is also provided which is designed to contact and seal the cartridge vent which is shown at 80 in FIG. 8, 110 in FIG. 11 and not shown on the cartridge in FIG. 15.

Figure 26:
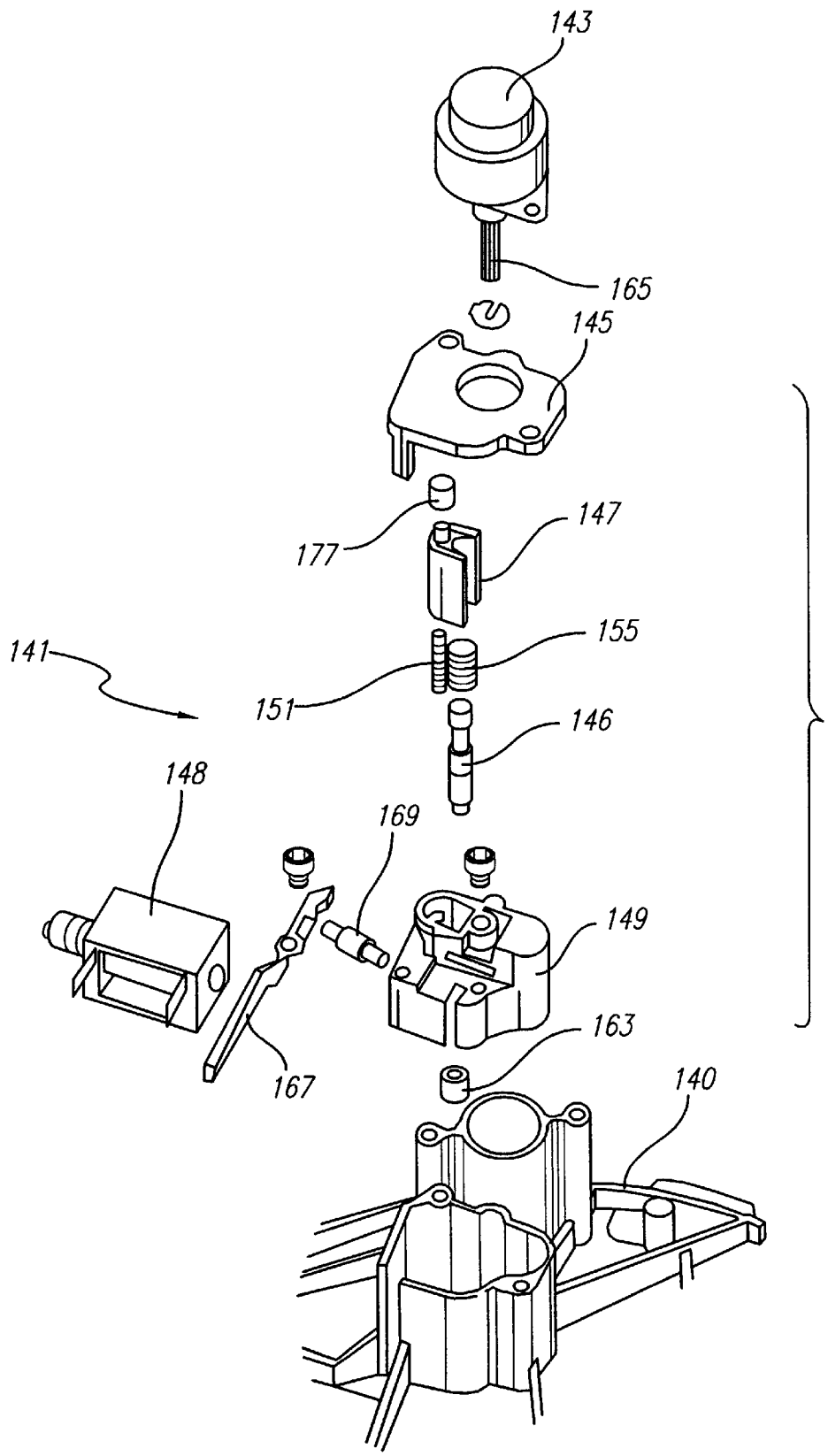
FIG. 26 is an exploded view of the preferred exemplary sample transport actuator system in accordance with the present invention.
Figure 27:
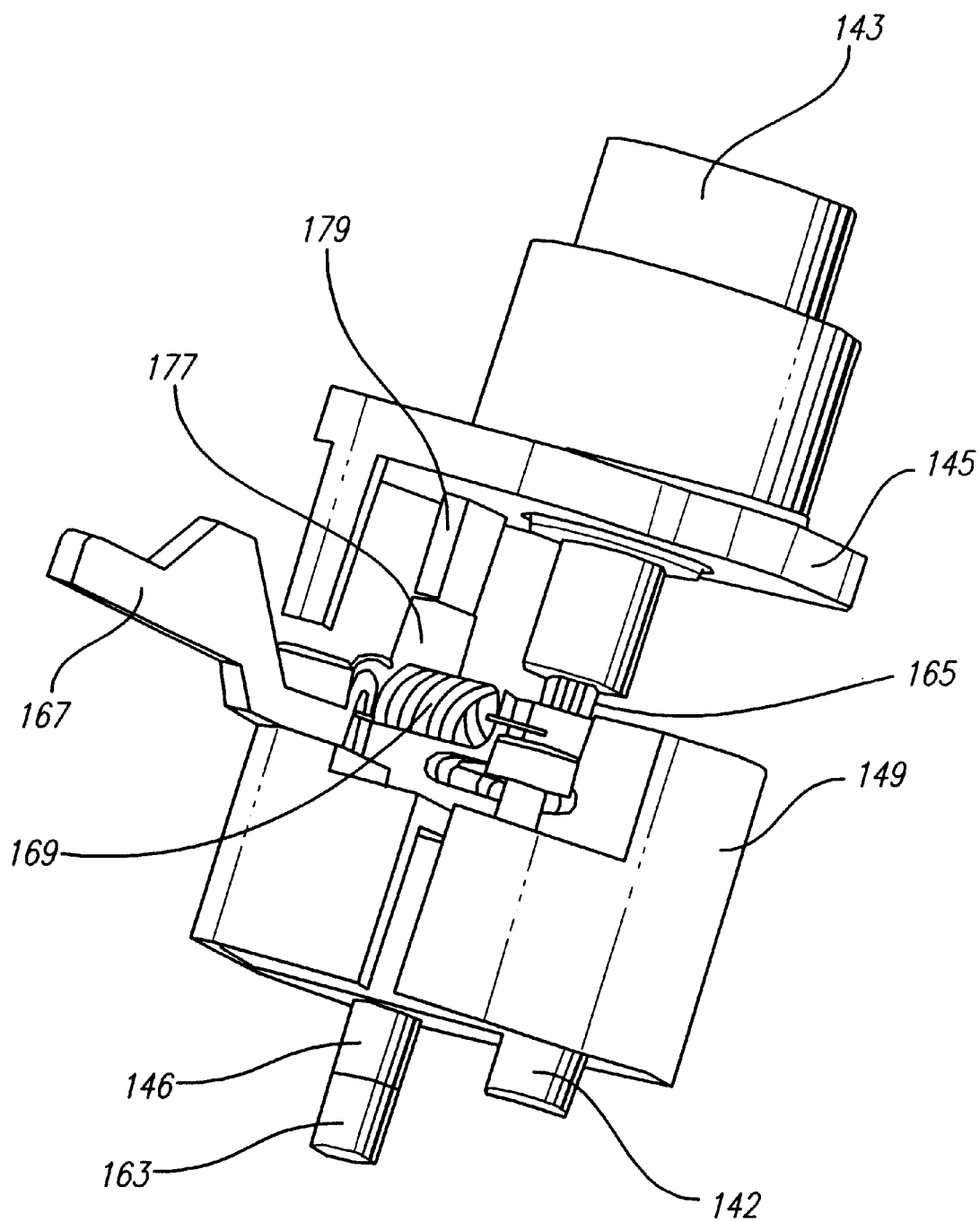
FIG. 27 is a perspective view of the assembled sample transport actuator.
Figure 28:
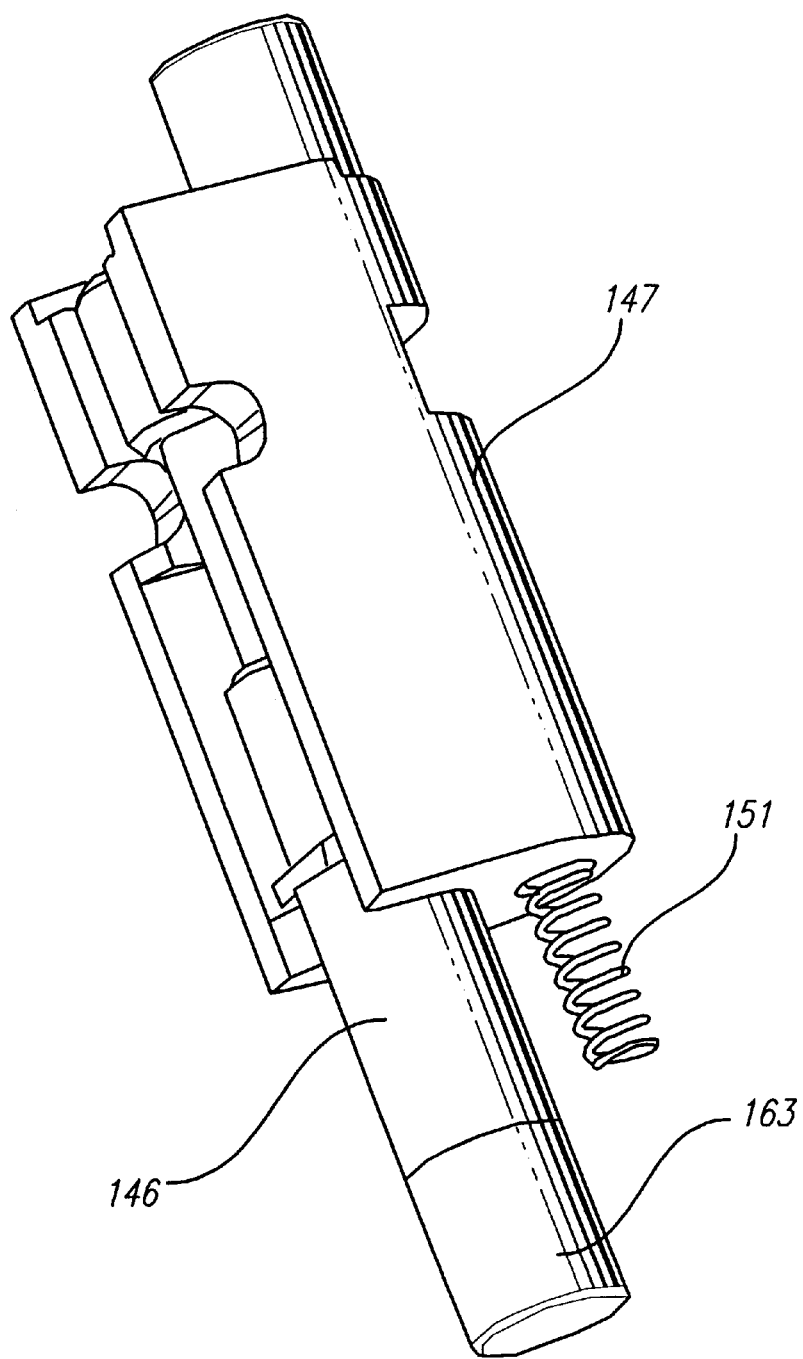
FIG. 28 shows vent actuator block which forms part of the sample transport actuator mechanism.

As best shown in FIGS. 26–28, the sample transport actuator mechanism 141 includes a motor 143, pusher cover 145, vent block 147, main pusher block 149, vent block spring 151 and vent seal rod spring 155. The vent seal rod 146 includes a tip 163. The block 149 is moved up and down by motor 143 via drive shaft 165. As best shown in FIG. 27, the vent seal rod tip 163 extends below the tip of the septum actuator rod 142. As a result, the vent seal rod tip 163 contacts and seals the cartridge vent prior to the septum actuator rod 142 compressing the flexible septum. It is necessary that the cartridge vent be closed prior to compression of the flexible septum. Otherwise, adequate pressurization of the cartridge may not be achieved to provide desired sample transport.

In addition, the sample transport actuator mechanism 141 must also provide for retraction of vent seal rod 146 from its sealing position against the cartridge prior to retraction of the septum actuator rod 142. By retracting the vent seal rod 146 first, pressure within the analytical cartridge is released uniformly. This eliminates the possibility of disturbing liquids within the cartridge plumbing due to premature movement of the flexible septum back to the septum's initial relaxed position. A wide variety of different possible mechanisms are possible to achieve this condition wherein the vent seal rod provides a seal prior to septum compression and releases the seal prior to septum relaxation. However, it is preferred that a solenoid-operated release system be used as shown in FIGS. 26 and 27. This system employs a solenoid 148 which operates a push lever 167 which is connected to seal rod 146 by lever spring 169. Operation of solenoid 148 moves lever 167 which releases the vent seal rod 146 so that it moves upward in vent block 147. Once the vent seal rod 146 is released, the main pusher block 149 is withdrawn to release the septum rod 142 from contact with the cartridge septum. To reset the vent seal, the vent seal rod 146 is moved to the position shown in FIG. 27, where a reset pin 177 is pushed against reset bar 179.

Figure 29:
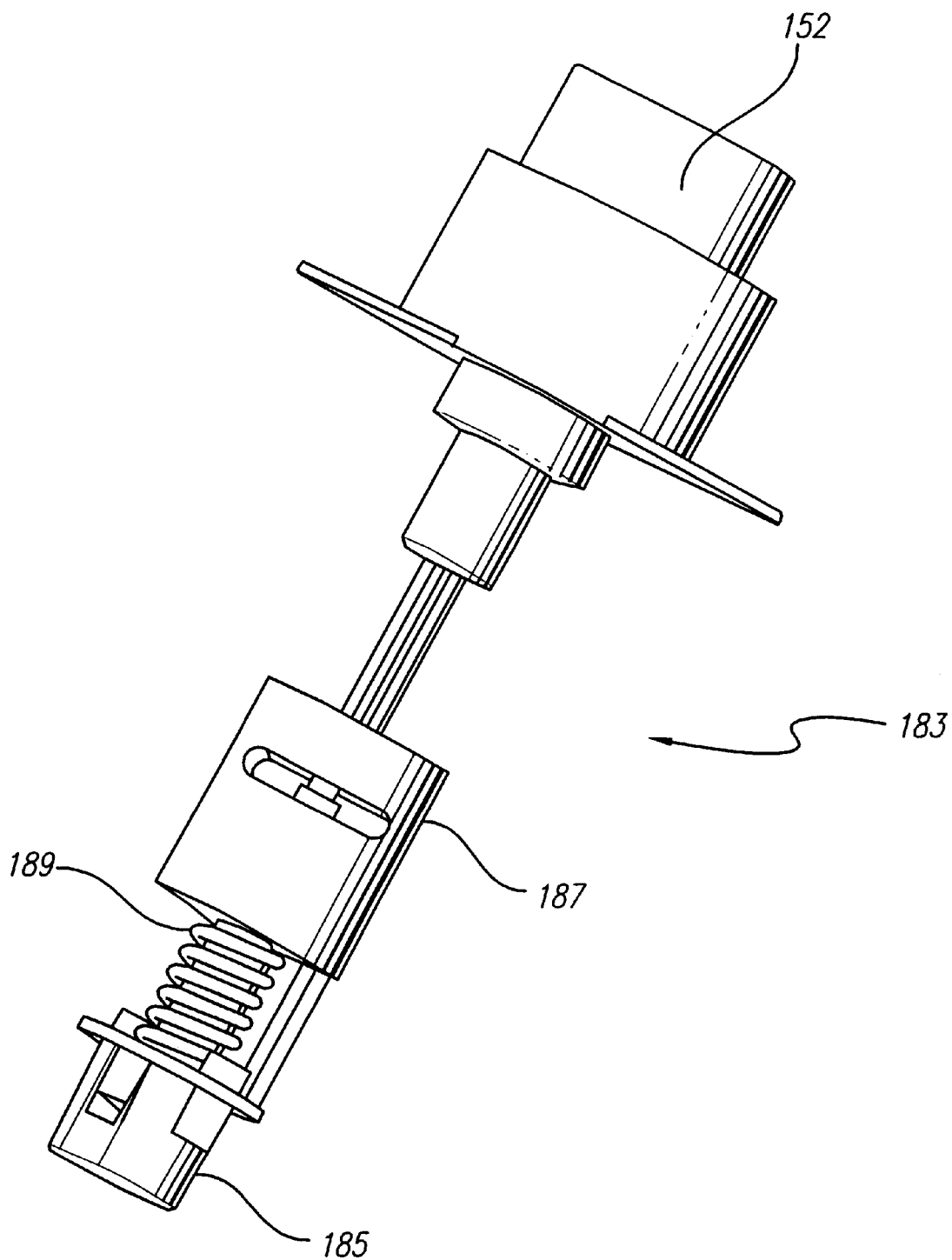
FIG. 29 shows the preferred exemplary reagent pouch actuator and related actuating mechanism.
Figure 30:
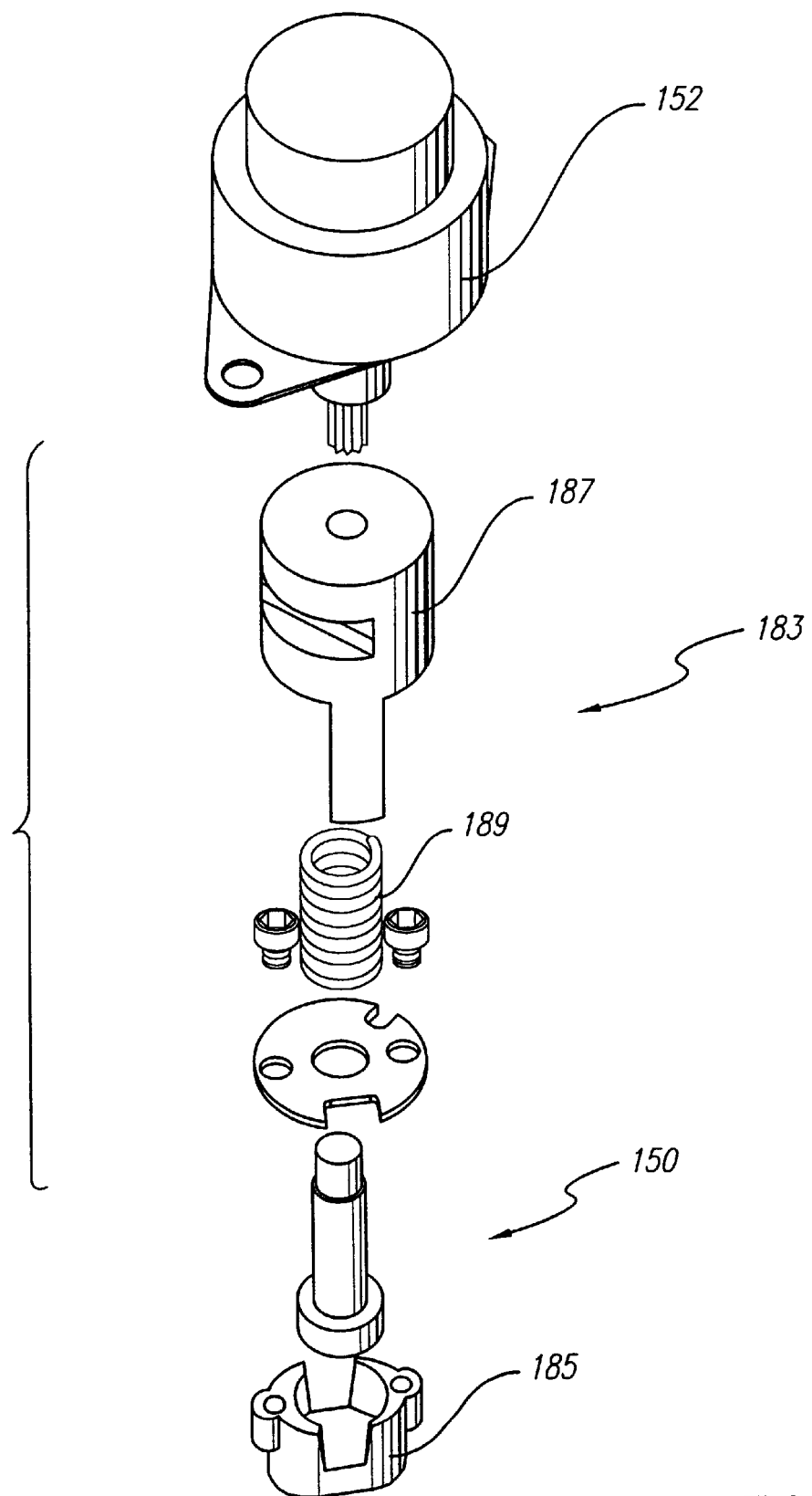
FIG. 30 is an exploded view of the reagent pouch actuator assembly shown in FIG. 29.

A reagent transport actuator is shown generally at 183 in FIGS. 18, 29 and 30. The reagent actuator 183 includes a reagent pouch actuator rod 150. The reagent actuator rod 150 is controlled by actuator motor 152. The rod 150 and actuator motor 152 form a reagent actuator mechanism which moves the reagent pouch on the analytical cartridge from a relaxed position to one or more compressed positions. A tip 185 is placed over the rod 150. The tip 185 is connected to a block 187. A spring 189 biases the tip 185 away from rod 150. During compression of the reagent pouch, the spring 189 becomes slightly compressed as the tip 185 is seated against the rod 150.

During compression of the reagent pouch, a spike or other element in the cartridge punctures the reagent cartridge to allow release and pressurized transport of the reagent. The spring 189 provides a constant pressure bias against the pouch even as it is punctured and releases fluid. The reagent actuator rod 150, septum actuator rod 142 and vent seal rod 146 are all shown in their retracted position in FIG. 18. The various rods are moved into contact with the cartridges as controlled by the tracking and control system of the instrument. The system is coordinated so that the actuator rods only move into contact with a cartridge when the cartridge rotor plate 32 is stationary. If desired, additional reagent pouch actuators and associated actuator mechanisms may be included in the instrument to handle cartridges which may have two or more reagent pouches which require simultaneous actuation.

Figure 32:
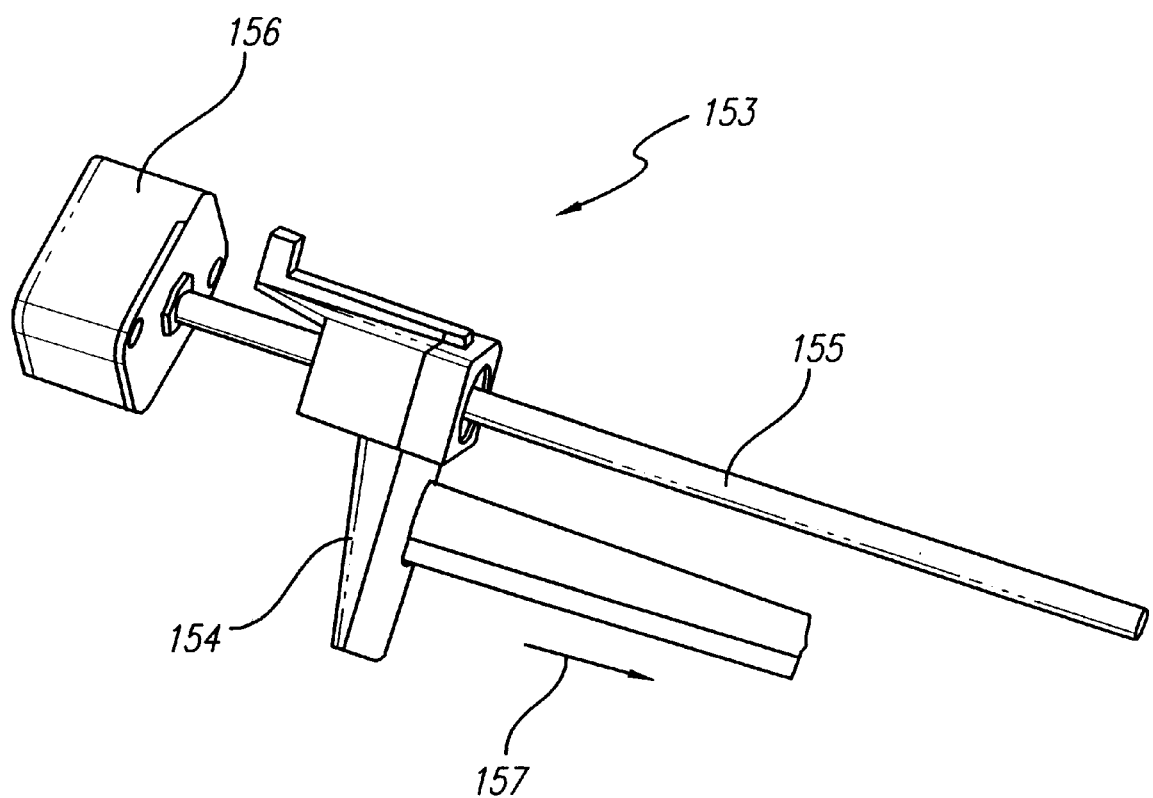
FIG. 32 is a detailed view of the sample cartridge ejection mechanism.

Ejection of cartridges 12 from rotor plate 32 is accomplished by an ejection mechanism which is shown at 153 in FIGS. 18 and 32. The mechanism 153 includes an ejection arm 154, guide rod 155 and drive motor 156. The actuator arm 154 is shown in a retracted position. The actuator arm 154 moves in the direction of arrow 157. The ejection actuator arm 154 is operated by motor mechanism 156. The actuator arm 154 ejects the cartridge 12 by first moving inner tabs 64 outward. Movement of inner tabs 64 outward also moves arms 53 and attached tabs 52 outward to release cartridge 12. The actuator arm 154 continues to move outward to move the counter weight 54 to the position shown in FIG. 7 and eject cartridge 12. The tracking and control unit of the instrument controls the ejection mechanism 153 and rotary drive mechanism 34 so that the cartridges are only ejected when they are located at ejection port 159 (see FIGS. 2 and 4).

A magnetic mechanism 161 is located adjacent to the ejector 153. The magnet 161 is used in combination with magnetic particles which may be included in the cartridges to provide mixing of reagents and samples within the cartridges as they pass by the magnet.

Figure 19:
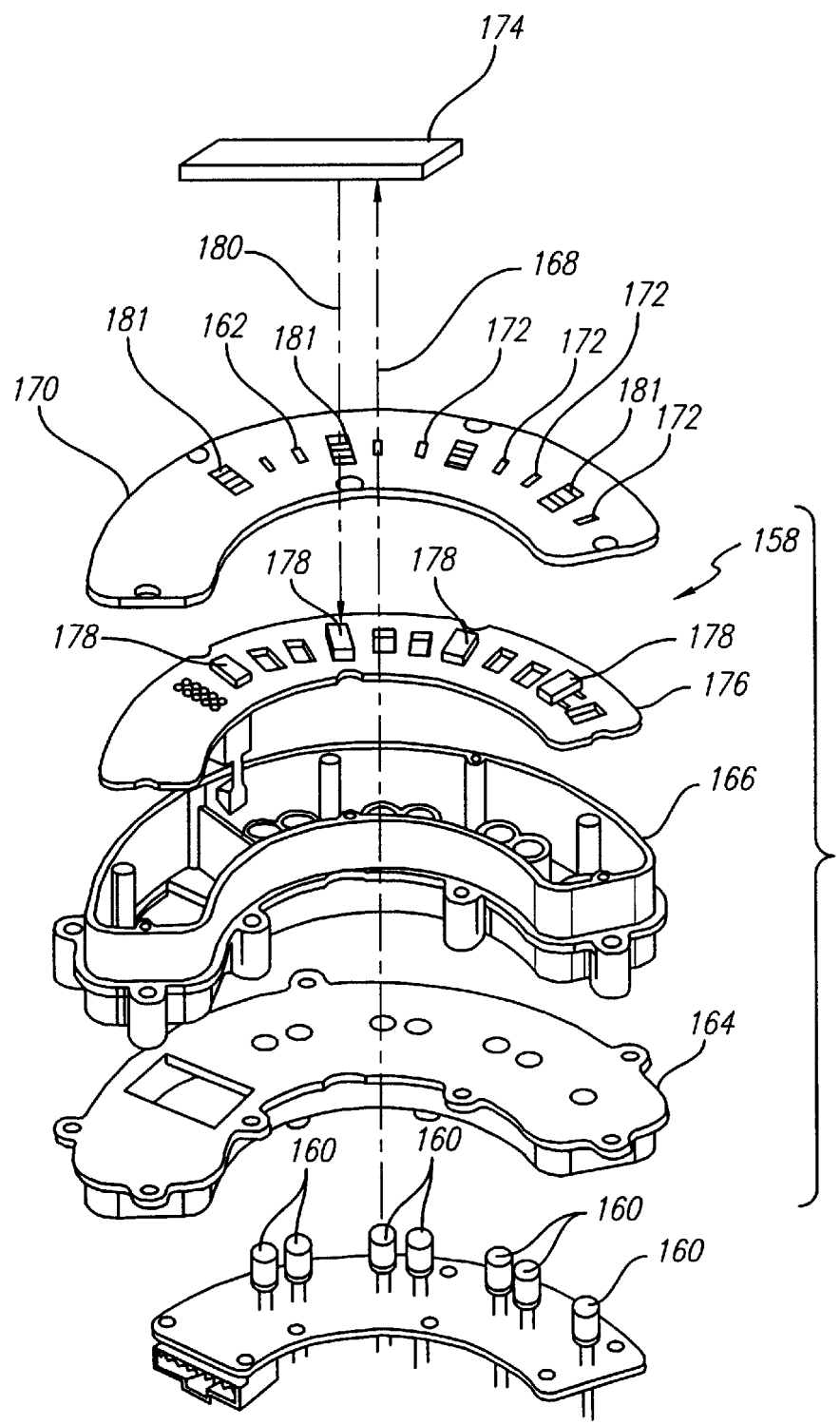
FIG. 19 is an exploded view of the optical detection unit which is located at a position within the analytical instrument below the cartridge rotor plate.

A preferred exemplary optical detector is shown at 158 in FIG. 19. The optical detector 158 is located directly below the cartridge carousel assembly 26. The optical detector 158 includes seven LED's 160. The optical detector 158 further includes collimator elements 164 and 166 which direct spectral radiation from the LED upward through the detector as represented by phantom line 168. The radiation path for only the central LED is shown. The collimating elements 164 and 166 direct the other LED beams in the same manner. The detector 158 further includes a beam control plate 170 which includes six slits 172 and one smaller slit 162. The slits 172 and 162 further reduce the size of LED beams 168 so that the final radiation beams 168 which contacts the test element of the analytical cartridge has a small cross-sectional area. The test element of the analytical cartridge is shown diagrammatically at 174 in FIG. 19. The slit 162 is smaller than the other slits and is designed for use with cartridges that include a cuvette.

The test element, as described above, may include either a reflectance test element or a transmittance test element (i.e., the cuvette 124 shown in FIGS. 16 and 17). The optical detector 158 further includes a return beam detector plate 176 which includes four optical detector elements 178. The return beam from analytical cartridge 174 travels through openings 181 in beam control plate 170. The path of the returning beam of transmitted or reflected spectral radiation is shown in phantom at 180. Again, for simplicity, the return beam path 180 is shown for only one of the LED's 160.

A wide variety of radiation sources may be utilized. In the preferred exemplary embodiment, the light-emitting diodes 160 each have a different wavelength. For example, moving from right to left in FIG. 19, the light-emitting diodes will have wavelengths of 425 nanometers, 505 nanometers, 570 nanometers, 590 nanometers, 615 nanometers, and 655 nanometers. The LED 160 on the far left is used for cuvette cartridges and preferably emits a wavelength of 570 nm. This range of LED wavelengths is preferred since it provides measurement beams ranging from near-ultraviolet through the visible spectrum to near-infrared wavelengths. A wide variety of LED combinations is possible depending upon the types of tests being conducted. The tracking and control unit is programmed, depending upon the particular test cartridge being analyzed, to expose the cartridge to one or more of the LED wavelengths. In this way, a wide variety of spectrophotometric measurements can be made.

As shown in FIG. 19, the optical detector 158 is arcuate in shape. The arcuate shape of the optical detector 158 is matched to the arcuate path of the cartridges as they move during rotation of the cartridge rotor plate 32. In this way, measurements may be taken when the cartridge is stationary or when the cartridge is moved past the detector during rotation of the rotor plate 32. The instrument may be programmed so that multiple measurements of the test element 174 may be made as it moves past the optical detector slits 172. In this way, measurements from one end of the test element to the other can be taken as the test element moves past a particular slit 172. Alternatively, the cartridge test element 174 may be held stationary over the optical detector 158 and time-dependent changes in spectral transmittance or reflectance may be measured. It is preferred that the cross-sectional area of slits 172 be substantially less than the cross-sectional area of the optically-accessible portion of the test element 174 present in the analytical cartridge. For example, the cross-sectional area of slit 172 should be at least one-tenth of the cross-sectional area of the optically-accessible portion of test element 174. Test beams having cross-sectional areas which are on the order of one-hundredth of the cross-sectional area of the optically-accessible portion of the test element are also possible.

Figure 20:
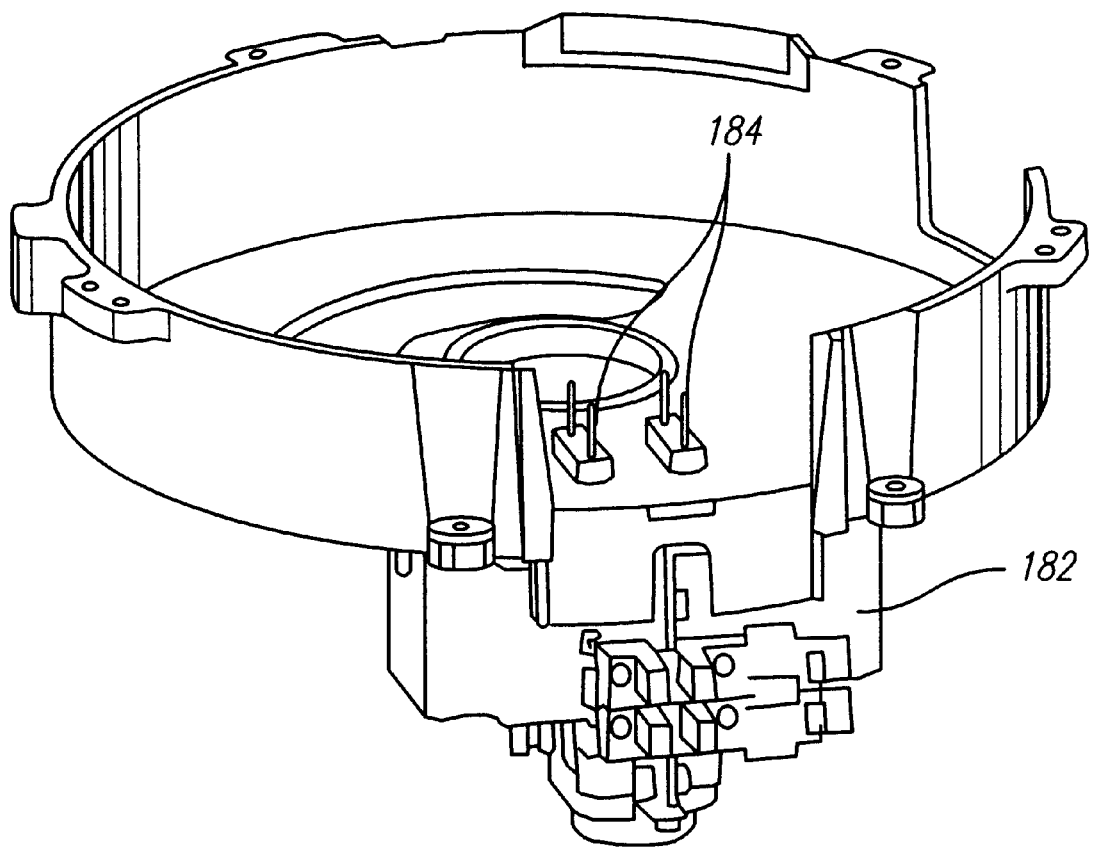
FIG. 20 shows the elements of the electrochemical detection system which are located in the lower housing of the preferred exemplary instrument.
Figure 21:
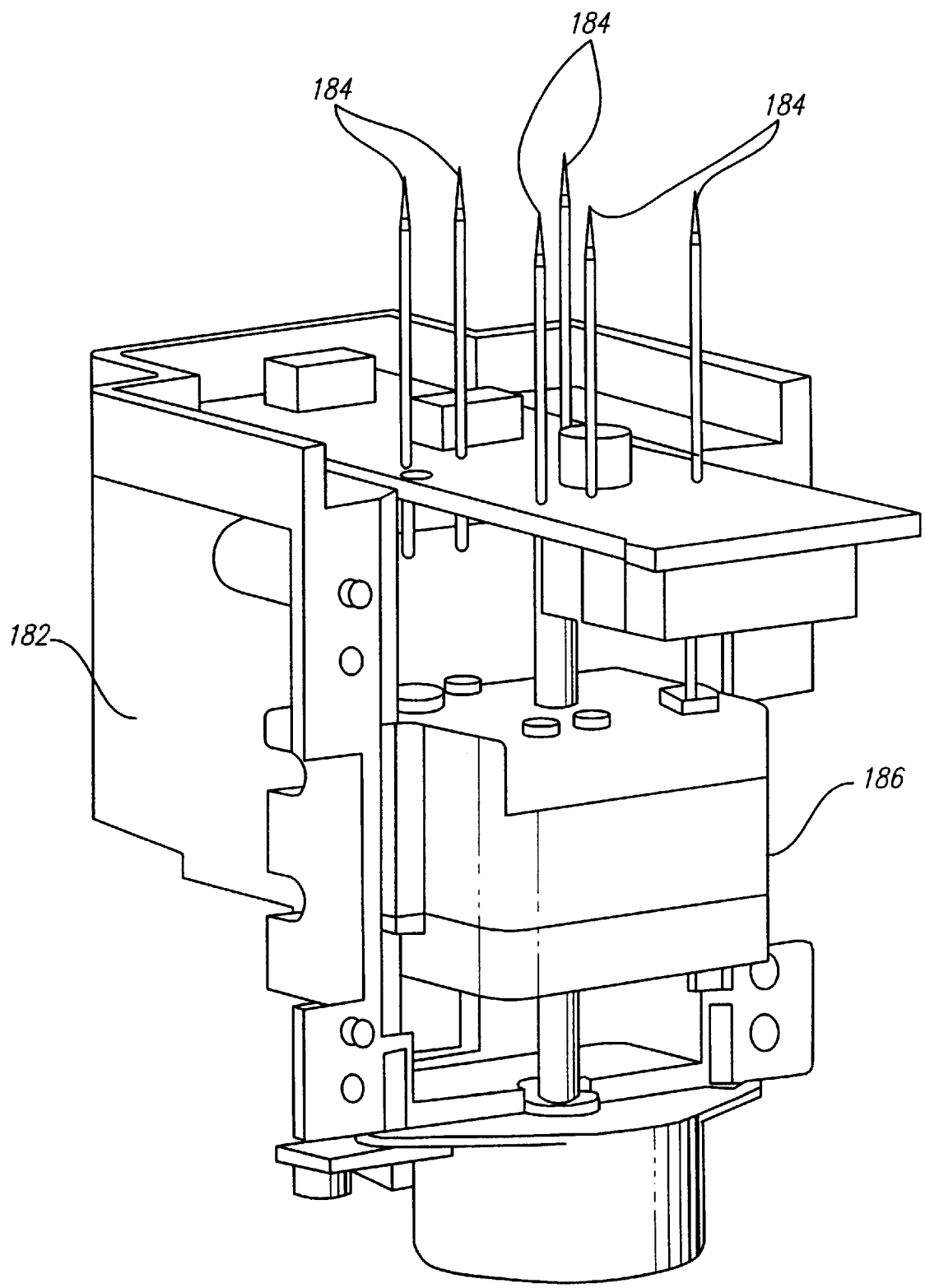
FIG. 21 is a more detailed view of FIG. 20 showing the electrochemical contact pins and actuator assembly.

A preferred exemplary electrochemical detector is shown at 182 in FIGS. 20 and 21. The electrochemical detector 182 is located directly below the cartridge carousel assembly 26 as shown in FIGS. 2 and 4. The electrochemical detector 182 includes electrical contact probes 184 which are designed to be moved by actuator mechanism 186 into contact with the electrochemical detector 100 located on the bottom of electrochemical cartridge 88 (FIG. 14). The instrument tracking and control system is set up so that the electrical probes 184 are only moved into position by actuator 182 when an electrochemical cartridge is being tested. Further, the instrument is programmed so that the electrical probes 184 are only moved into position when the cartridge is located over the electrochemical detector 182 and is stationary.

Figure 22:
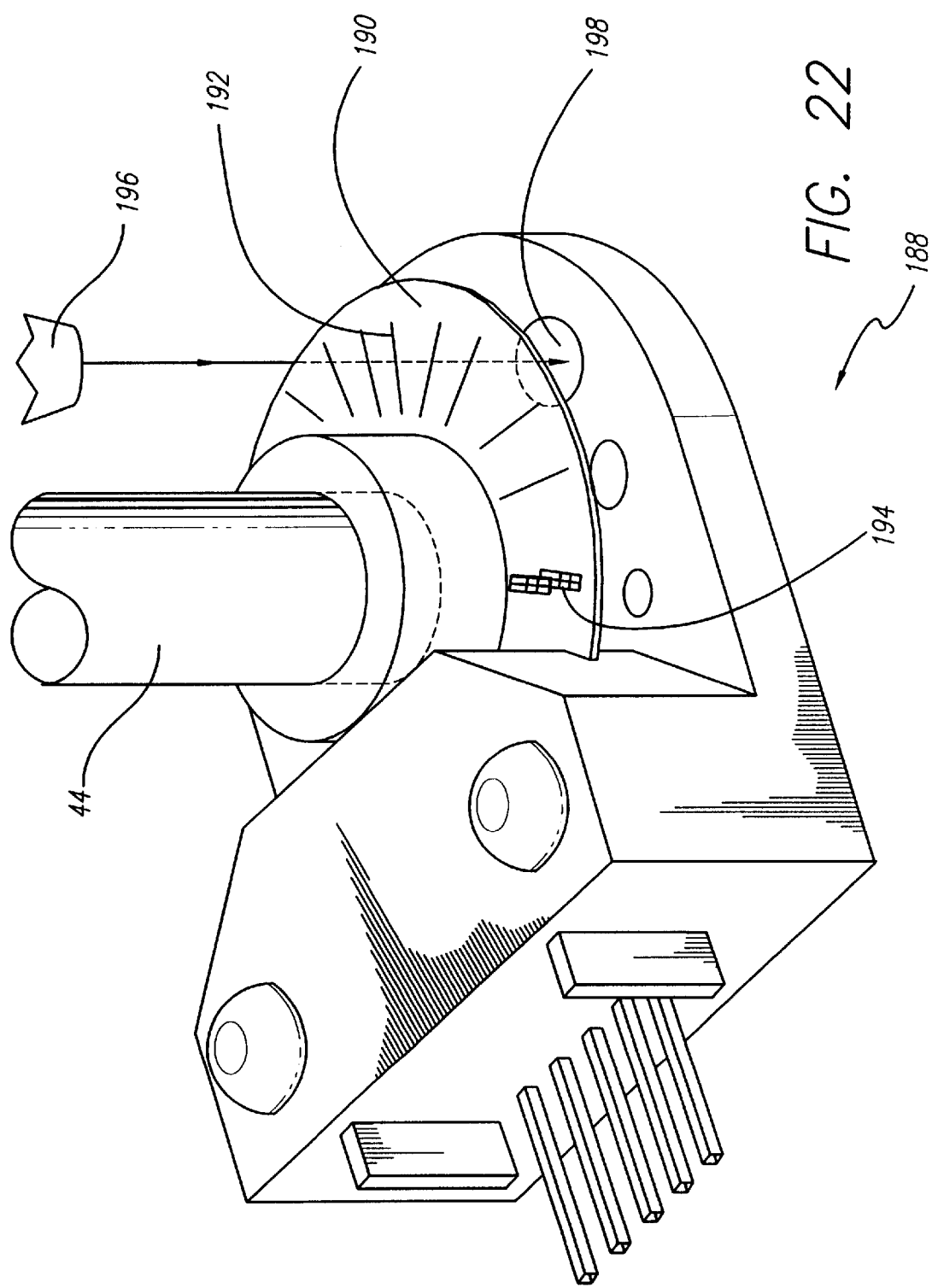
FIG. 22 shows the encoding assembly located in the bottom portion of the instrument which provides tracking and control of the cartridge rotor plate.
Figure 23:
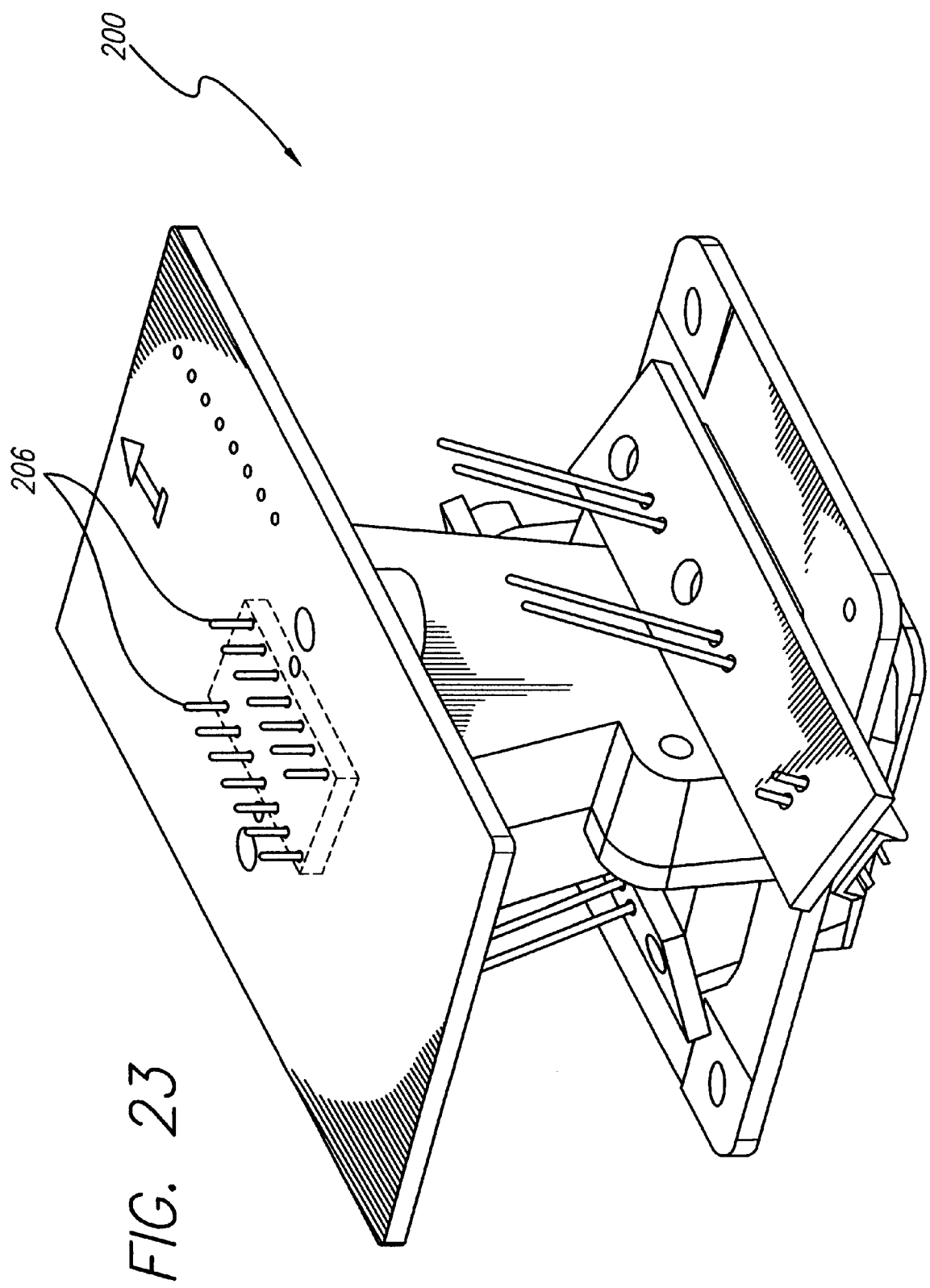
FIG. 23 is a perspective view of the bar code reader which is located in the top portion of the instrument.
Figure 24:
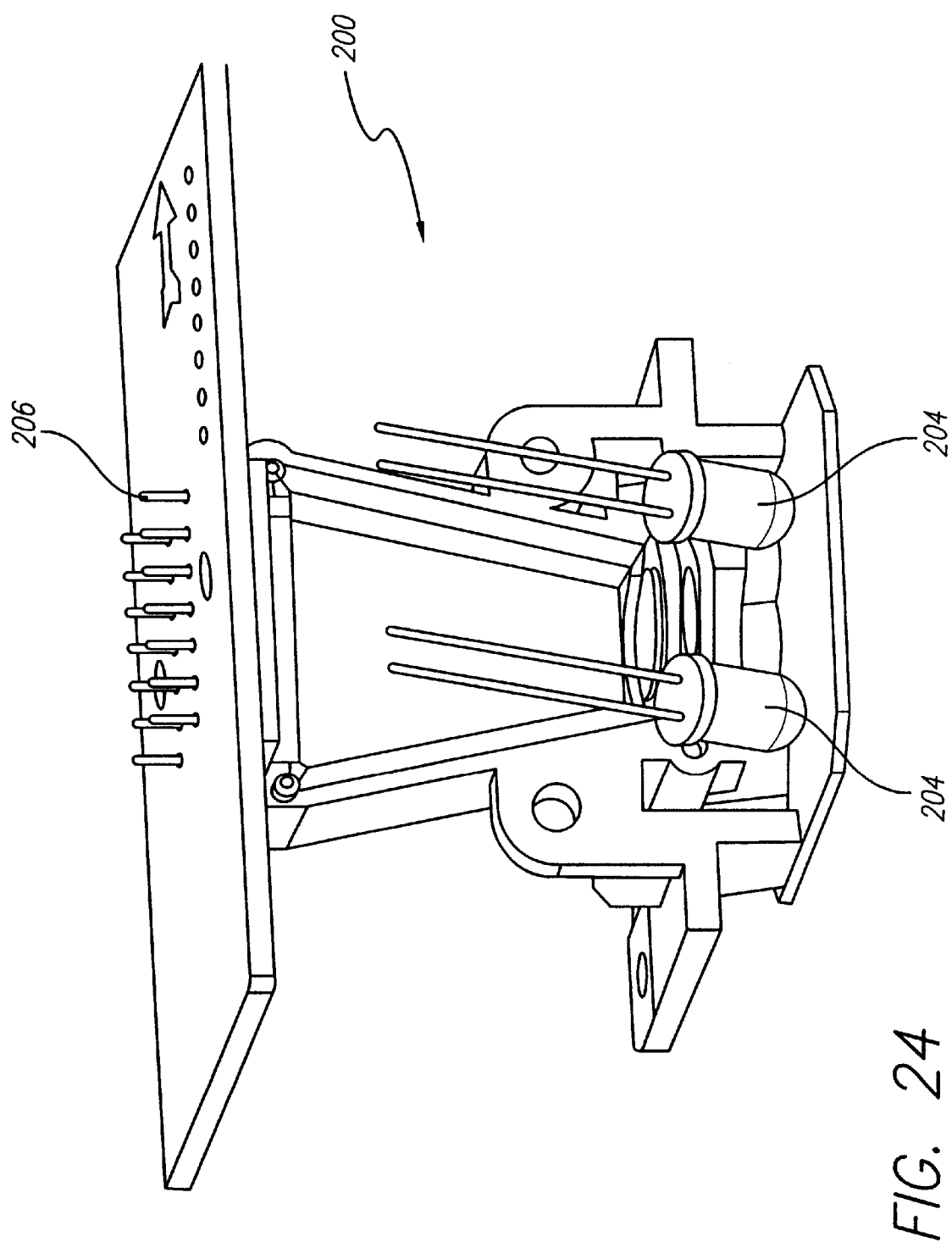
FIG. 24 is an alternate perspective view of the bar code reader shown in FIG. 23 with the light-emitting diodes (LED) on one side being exposed.

As part of the tracking and control system, the analytical instrument will preferably include a spindle positioning encoder which is shown at 188 in FIG. 22, and more generally at 46 in FIG. 5. The encoder is connected to the circuit boards of the tracking and control unit 30 which are in turn connected with the central processing unit. The encoder 188 is connected to spindle 44 which in turn is connected to the rotor plate 32. A transparent optical disk 190 is provided which has indexing marks 192 which include a home index mark 194. A light source 196 with corresponding optical detector 198 are provided to detect passage of the index marks past the optical detector. The combined light source and optical detector 196 and 198 provides continual input to the real-time processing unit and central processor which allows accurate control of rotation speeds and radial location of cartridges, when they are located within the cartridge rotor plate. Other encoder systems are possible provided that they are capable of providing the same tracking information which is input into the tracking and control system in order to accurately control rotation and positioning the cartridge rotor plate 32.

The analytical instrument includes a bar code reader which is shown at 200 in FIGS. 2–3 and 23–24. The bar code reader 200 scans arcuate bar codes 201 on the analytical cartridges to provide input into the tracking and control system regarding the type of cartridge and tests to be run (see FIG. 6). The bar code reader 200 also reads a Z-shaped position calibration label 202 on the rotor plate 32 (FIG. 6). The bar code reader 200 preferably utilizes a 1:1 ratio double-lens camera and a light source such as LED's 204. The bar code reader also includes a photodiode light detector 206. As the alternating light and dark segments of the bar code 201 pass before the bar code reader 200, they are illuminated by the light source 204 and projected onto the photodiode detector chip 206 as a series of light pulses. The detector chip 206 is preferably a linear array of 128 photodiode elements oriented such that light reflected from each bar code element shines upon about three or more photodiode elements. The bar code reader 200 is also adapted to scan the Z-shaped position calibration label 202 on the spinning rotor plate 32. The bar code reader 200 in conjunction with the encoder 188 provide input into the central processing unit and/or real-time processor which allows the position of the rotor plate to be accurately determined and controlled.

Figure 25:
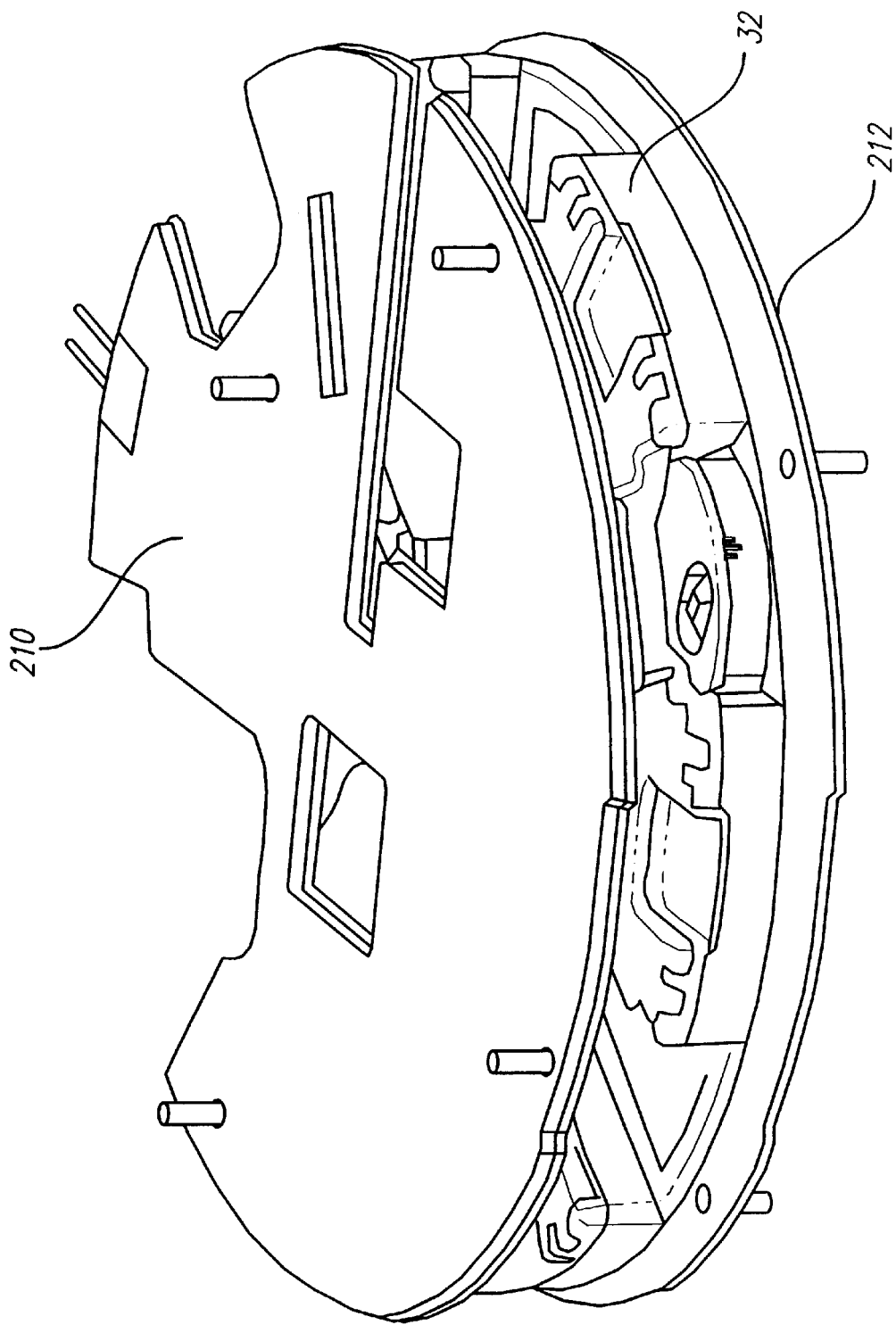
FIG. 25 is a perspective view of the housing plates which surround the cartridge rotor plate. The housing plates include heating elements which are operated to maintain controlled temperature during processing of the cartridges.

It is preferred that the cartridge rotor plate be maintained at constant temperature. For many cartridges, test results will vary if the temperature is not kept constant. In addition, some tests must be conducted at elevated temperatures. Accordingly, it is preferred that two heating plates 210 and 212 be located on either side of the cartridge rotor plate 32 as shown in FIG. 25. The heater plates or platens are preferably electrically heated. However, other types of temperature control systems may be used. The spinning of the rotor plate at relatively high speeds (e.g. 1500 rpm) facilitates heating because of the uniform and constant mixing of air and heat generated by the rotor.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

What is claimed is:

1. An analytical instrument for analyzing fluid sample in an analytical cartridge, said cartridge having a sample metering/separation system that is operated by centrifugal force, a sample transport system that is operated by pressure and a test element which provides a detectable property of said fluid sample, said sample transport system including a flexible septum that can be moved from a relaxed position to one or more compressed positions wherein movement from said relaxed position to said one or more compressed positions provides pressurization of said sample transport system and wherein said cartridge further includes a vent for said sample metering/separation system, said instrument comprising:

A) a cartridge carousel assembly which receives one or more of said analytical cartridges, said cartridge carousel assembly comprising:
  a) a cartridge rotor plate which comprises a center and a plurality of cartridge ports which are located in spaced relation radially outward from said center, said cartridge ports being shaped to receive said cartridges; and
  b) a rotary drive mechanism which rotates said cartridge rotor plate about the center thereof, wherein rotation of said cartridge rotor plate activates said centrifugal force operated sample metering/sample system;

B) a sample transport actuator which activates the pressure operated sample transport system of said cartridge, said sample transport actuator comprising:
  a septum actuator having a surface which is movable into contact with said flexible septum of said cartridge to move said septum from said relaxed position to said one or more compressed positions when said cartridge is located in said cartridge carousel assembly, said septum actuator comprising a septum rod comprising a tip which comprises said surface which is movable into contact with said septum;
  a vent seal element having a surface which is movable to a position which seals said vent, said vent seal element comprising a seal rod comprising a tip which comprises said surface which seals said vent; and
  a sample actuator mechanism which jointly moves said septum actuator and vent seal element to provide movement of said flexible septum and sealing of said vent wherein said vent is sealed prior to movement of said septum from said relaxed position to said one or more compressed positions and wherein said vent is unsealed prior to movement of said septum from said one or more compressed positions to said relaxed position, said sample actuator mechanism comprising:
    a connector block which connects said septum rod to said seal rod to provide joint movement of said septum rod and said seal rod, said seal rod being oriented relative to said septum rod such that said seal rod tip contacts said vent on said cartridge prior to compression of said septum by said septum rod; and
    an actuator motor which moves said connector block so that said septum rod and seal rod move jointly between retracted positions and extended positions;
    a release mechanism connected to said seal rod wherein said release mechanism withdraws said seal rod tip from contact with said vent prior to movement of said connector block to withdraw said septum rod from contact with said septum;

C) a detector which measures said detectable analytical property of said fluid sample which is provided by the test element of said cartridge when said cartridge is located in said cartridge carousel assembly; and D) a tracking and control unit which tracks and controls said rotary drive mechanism and sample transport actuator, said tracking and control unit comprising a user input interface for receiving data input from a user of the instrument, a central processing unit, a real time processor and a data output interface which provides output of results of the measurements made by said detector.

2. An analytical instrument for analyzing fluid sample in an analytical cartridge according to claim 1 wherein said instrument further comprises a reagent transport actuator which activates a pressure operated reagent transport system which is present in said cartridge and wherein said tracking and control unit provides tracking and control of said rotary drive mechanism, pressure operated sample transport system and pressure operated reagent transport system wherein said coordinated operation provides delivery of a metered amount of sample fluid and an aliquot of reagent to the test element of said cartridge.

3. An analytical instrument for analyzing fluid sample in an analytical cartridge according to claim 1 wherein said cartridge includes a reagent transport system that includes a flexible pouch that can be moved from a relaxed position to one or more compressed positions to provide movement of reagent within said cartridge, said instrument further comprising a reagent transport actuator that activates said reagent transport system when said cartridge is located in said cartridge carousel assembly said reagent transport actuator comprising:
 a reagent pouch actuator having a surface which is movable into contact with said reagent pouch of said cartridge when said cartridge is located in said cartridge carousel assembly to move said pouch from said relaxed position to one or more of said compressed positions; and
 a reagent actuator mechanism that moves said reagent pouch actuator into contact with said reagent pouch to provide movement of said pouch from said relaxed position to one or more of said compressed positions.

4. An analytical instrument for analyzing fluid sample in an analytical cartridge according to claim 3 wherein said reagent pouch actuator comprises a reagent rod comprising a tip which comprises said surface which is movable into contact with said reagent pouch and said reagent actuator mechanism comprises a reagent actuator motor which moves said reagent rod between a retracted position and extended positions where said reagent rod tip is in contact with said reagent pouch.

5. An analytical instrument for analyzing fluid sample in an analytical cartridge according to claim 1 wherein said cartridge ports each comprise a cartridge dock which is shaped to receive said cartridges and a balance weight dock which is located radially inward from said cartridge dock, said cartridge dock being shaped to receive a balance weight, said analytical instrument further comprising:
 a locking mechanism which holds said cartridge in said cartridge dock during rotation of said cartridge rotor plate;
 a balancing mechanism which comprises a balance weight wherein said balance weight is movable to said balance weight dock when said cartridge is inserted into said cartridge dock and wherein said balance weight remains in said cartridge dock during rotation of said cartridge rotor plate when a cartridge is not present in said cartridge dock;
 an ejection mechanism which ejects said cartridge from said cartridge port; and wherein said tracking and control unit tracks and controls said locking mechanism and said ejection mechanism.

6. An analytical instrument for analyzing fluid sample in an analytical cartridge according to claim 1 which is adapted for use with cartridges that have a top side, bottom side, and a test element which includes an optical element that is optically accessible form only one side of said cartridge and wherein said optical element provides an optically detectable analytical property of said fluid, said detector comprising:
 an optical detector which measures said detectable analytical property of said fluid sample which is provided by the optical element of said cartridge, said optical detector comprising:
  a) a radiation source located relative to said cartridge rotor to provide an incident beam of radiation which contacts said optical element and wherein a return beam of radiation is emitted by said optical element in response to contact by said incident beam of radiation; and
  b) a return beam detector which measures said return beam of radiation wherein said radiation source and return beam detector are both located on the same side of said cartridge when it is located within said cartridge rotor plate; and
 wherein said tracking and control unit tracks and controls said rotary drive mechanism and said detector to provide coordinated operation so that said optical detector can make measurements of said optical element while said cartridge rotor is stationary or rotating.

7. An analytical instrument according to claim 6 wherein said radiation source comprises:
 a plurality of light emitting diodes which are arranged to form an arcuate array of light emitting diodes which corresponds to the arcuate path of said optical element as said cartridge travels in said cartridge rotor plate during rotation of said cartridge rotor plate.

8. An analytical instrument according to claim 6 wherein said radiation source comprises one or more light emitting diodes which emit radiation in a wavelength selected from the group consisting of ultra-violet, visible and infra-red.

9. An analytical instrument according to claim 8 wherein said radiation source comprises:
 a first light emitting diode which emits radiation consisting of a wavelength of about 425 nanometers;
 a second light emitting diode which emits radiation consisting of a wavelength of about 505 nanometers;
 a third light emitting diode which emits radiation consisting of a wavelength of about 570 nanometers;
 a fourth light emitting diode which emits radiation consisting of a wavelength of about 590 nanometers;
 a fifth light emitting diode which emits radiation consisting of a wavelength of about 615 nanometers; and
 a sixth light emitting diode which emits radiation consisting of a wavelength of about 655 nanometers.

10. An analytical instrument according to claim 6 wherein the optically accessible portion of said optical element has a cross-sectional area and wherein said radiation source comprises a collimator which directs said incident beam of radiation onto said optical element as a collimated incident beam which has a cross-section which is substantially less than the cross-section of said optically accessible portion.

11. An analytical instrument according to claim 10 wherein said radiation source comprises multiple collimators wherein said radiation source comprises multiple collimators wherein the cross-sections of said collimated incident beams are not the same.

12. An analytical instrument according to claim 10 wherein said tracking and control unit is set to take multiple measurements of the optical element by exposing said optical element to a plurality of collimated incident beams and measuring the resultant plurality of return beams.

13. An analytical instrument for analyzing fluid sample in an analytical cartridge according to claim 1 which is adapted for use with cartridges that have a top side, bottom side, and a test element which includes an electrochemical element that is electrically accessible from only one side of said cartridge and wherein said electrochemical element provides an electrically detectable analytical property of said fluid, said detector comprising:

an electrical detector which measures said electrically detectable analytical property of said fluid sample which is provided by the electrochemical element of said cartridge when said cartridge is located in said carousel assembly, said electrochemical detector comprising:

a) an electrical probe comprising a surface which is movable between a retracted position and an extended position where said electrical probe is in contact with said electrochemical element to provide measurement of said electrically detectable analytical property; and b) a probe actuator assembly which moves said electrical probe between said retracted position and said extended position; and wherein said tracking and control unit tracks and controls said rotary drive mechanism and said electrical detector to provide coordinated operation so that said electrical detector can make measurements of said electrochemical element while said cartridge rotor is stationary.

\* \* \* \* \*

UNITED STATES PATENT AND TRADEMARK OFFICE
CERTIFICATE OF CORRECTION

PATENT NO. : 6,348,176 B1
DATED : February 19, 2002
INVENTOR(S) : Hammer et al.

It is certified that error appears in the above-identified patent and that said Letters Patent is hereby corrected as shown below:

Column 4,
Line 50, "U.S. Pat. No. Design. 424,1956" should be -- U.S. Pat. No. Design 424,956 --;
Line 62, "PCT/US99/0628." should read -- PCT/US99/06287 --.

Signed and Sealed this

Seventh Day of February, 2006

JON W. DUDAS
*Director of the United States Patent and Trademark Office*